US012566177B2

(12) United States Patent
Chang et al.

(10) Patent No.: US 12,566,177 B2
(45) Date of Patent: Mar. 3, 2026

(54) ANTIGEN AND ANTIBODIES PREPARED BASED ON PADI4 SERVING AS TUMOR MARKER, AND APPLICATION THEREOF

(71) Applicant: SHANDONG XINCHUANG BIOLOGICAL TECHNOLOGY CO., LTD., Jinan (CN)

(72) Inventors: Xiaotian Chang, Jinan (CN); Xueyan Lv, Jinan (CN); Dongxia Yang, Jinan (CN); Yanqiu Xing, Jinan (CN); Yuxia Gao, Jinan (CN); Shili Shao, Jinan (CN); Feng Liu, Jinan (CN); Junchao Feng, Jinan (CN); Jun Xing, Jinan (CN); Lin Li, Jinan (CN)

(73) Assignee: SHANDONG XINCHUANG BIOLOGICAL TECHNOLOGY CO., LTD., Jinan (CN)

( * ) Notice: Subject to any disclaimer, the term of this patent is extended or adjusted under 35 U.S.C. 154(b) by 944 days.

(21) Appl. No.: 17/662,422

(22) Filed: May 7, 2022

(65) Prior Publication Data

US 2022/0268777 A1      Aug. 25, 2022

Related U.S. Application Data

(63) Continuation of application No. PCT/CN2020/112240, filed on Aug. 28, 2020.

(51) Int. Cl.
*C07K 16/00* (2006.01)
*C07K 16/40* (2006.01)

*C12N 9/78* (2006.01)
*G01N 33/574* (2006.01)

(52) U.S. Cl.
CPC ....... *G01N 33/57488* (2013.01); *C07K 16/40* (2013.01); *C12N 9/78* (2013.01); *C12Y 305/03015* (2013.01); *G01N 2333/978* (2013.01)

(58) Field of Classification Search
None
See application file for complete search history.

(56) References Cited

U.S. PATENT DOCUMENTS

2018/0044434 A1 * 2/2018 Sato ........................ C12N 15/09

* cited by examiner

*Primary Examiner* — Celine X Qian
(74) *Attorney, Agent, or Firm* — CBM PATENT CONSULTING, LLC

(57) ABSTRACT

An antigen and antibodies prepared based on peptidylarginine deiminase (PADI4) serving as a tumor marker, and application thereof are disclosed. The antigen has an amino acid sequence shown as SEQ ID NO. 1. Specific antibodies prepared by using the antigen are also disclosed. The protein PADI4 monoclonal antibodies include a protein PADI4 monoclonal antibody coated onto an ELISA plate and a biotin-labeled protein PADI4 monoclonal antibody. A kit prepared by using the antibodies of the present disclosure can effectively and stably determine a protein PADI4 level of a human serum, and has a broad spectrum, detectability, and high test repeatability.

6 Claims, 11 Drawing Sheets
Specification includes a Sequence Listing.

■ represents a PADI4 expression level of a serum of a subject with malignant tumor, ▨ represents a PADI4 expression level of a serum of a postoperative subject with malignant tumor, ◩represents a PADI4 expression level of a serum of a subject with benign tumor in the same organ, □represents a PADI4 expression level of a serum of a control health subject.

■ represents a PADI4 expression level of a serum of a subject with malignant tumor, ▨ represents a PADI4 expression level of a serum of a postoperative subject with malignant tumor, ◨ represents a PADI4 expression level of a serum of a subject with benign tumor in the same organ, □ represents a PADI4 expression level of a serum of a control health subject.

represents a PADI4 expression level of a serum of a subject with malignant tumor, represents a PADI4 expression level of a serum of a postoperative subject with malignant tumor, □ represents a PADI4 expression level of a serum of a control health subject.

■ represents a PADI4 expression level of a serum of a subject with malignant tumor, ▨ represents a PADI4 expression level of a serum of a postoperative subject with malignant tumor, ◪ represents a PADI4 expression level of a serum of a subject with benign tumor in the same organ, ☐ represents a PADI4 expression level of a serum of a control health subject.

$$y = 0.09157\,x^2 + 16.31927\,x - 0.26599$$
$$R^2 = 0.99999$$

$$y = 19.87918\,x^2 - 15.49100\,x + 7.99383$$
$$R^2 = 0.96747$$

SEQUENCE LISTING

```
<160> NUMBER OF SEQ ID NOS: 12

<210> SEQ ID NO 1
<211> LENGTH: 695
<212> TYPE: PRT
<213> ORGANISM: Artificial Sequence
<220> FEATURE:
<223> OTHER INFORMATION: It is synthesized.

<400> SEQUENCE: 1

Met Gly Ala Ser Trp Ser His Pro Gln Phe Glu Lys Gly Gly Gly Ser
1               5                   10                  15

Gly Gly Gly Ser Gly Gly Ser Ala Trp Ser His Pro Gln Phe Glu Lys
                20                  25                  30

Met Ala Gln Gly Thr Leu Ile Arg Val Thr Pro Glu Gln Pro Thr His
            35                  40                  45

Ala Val Cys Val Leu Gly Thr Leu Thr Gln Leu Asp Ile Cys Ser Ser
        50                  55                  60

Ala Pro Glu Asp Cys Thr Ser Phe Ser Ile Asn Ala Ser Pro Gly Val
65                  70                  75                  80

Val Val Asp Ile Ala His Gly Pro Pro Ala Lys Lys Lys Ser Thr Gly
                85                  90                  95
```

-continued

```
Ser Ser Thr Trp Pro Leu Asp Pro Gly Val Glu Val Thr Leu Thr Met
            100             105             110

Lys Val Ala Ser Gly Ser Thr Gly Asp Gln Lys Val Gln Ile Ser Tyr
            115             120             125

Tyr Gly Pro Lys Thr Pro Pro Val Lys Ala Leu Leu Tyr Leu Thr Gly
    130             135             140

Val Glu Ile Ser Leu Cys Ala Asp Ile Thr Arg Thr Gly Lys Val Lys
145             150             155             160

Pro Thr Arg Ala Val Lys Asp Gln Arg Thr Trp Thr Trp Gly Pro Cys
            165             170             175

Gly Gln Gly Ala Ile Leu Leu Val Asn Cys Asp Arg Asp Asn Leu Glu
            180             185             190

Ser Ser Ala Met Asp Cys Glu Asp Asp Glu Val Leu Asp Ser Glu Asp
            195             200             205

Leu Gln Asp Met Ser Leu Met Thr Leu Ser Thr Lys Thr Pro Lys Asp
    210             215             220

Phe Phe Thr Asn His Thr Leu Val Leu His Val Ala Arg Ser Glu Met
225             230             235             240

Asp Lys Val Arg Val Phe Gln Ala Thr Arg Gly Lys Leu Ser Ser Lys
            245             250             255

Cys Ser Val Val Leu Gly Pro Lys Trp Pro Ser His Tyr Leu Met Val
            260             265             270

Pro Gly Gly Lys His Asn Met Asp Phe Tyr Val Glu Ala Leu Ala Phe
            275             280             285

Pro Asp Thr Asp Phe Pro Gly Leu Ile Thr Leu Thr Ile Ser Leu Leu
    290             295             300

Asp Thr Ser Asn Leu Glu Leu Pro Glu Ala Val Val Phe Gln Asp Ser
305             310             315             320

Val Val Phe Arg Val Ala Pro Trp Ile Met Thr Pro Asn Thr Gln Pro
            325             330             335

Pro Gln Glu Val Tyr Ala Cys Ser Ile Phe Glu Asn Glu Asp Phe Leu
            340             345             350

Lys Ser Val Thr Thr Leu Ala Met Lys Ala Lys Cys Lys Leu Thr Ile
            355             360             365

Cys Pro Glu Glu Glu Asn Met Asp Asp Gln Trp Met Gln Asp Glu Met
    370             375             380

Glu Ile Gly Tyr Ile Gln Ala Pro His Lys Thr Leu Pro Val Val Phe
385             390             395             400

Asp Ser Pro Arg Asn Arg Gly Leu Lys Glu Phe Pro Ile Lys Arg Val
            405             410             415

Met Gly Pro Asp Phe Gly Tyr Val Thr Arg Gly Pro Gln Thr Gly Gly
            420             425             430

Ile Ser Gly Leu Asp Ser Phe Gly Asn Leu Glu Val Ser Pro Pro Val
            435             440             445

Thr Val Arg Gly Lys Glu Tyr Pro Leu Gly Arg Ile Leu Phe Gly Asp
    450             455             460

Ser Cys Tyr Pro Ser Asn Asp Ser Arg Gln Met His Gln Ala Leu Gln
465             470             475             480

Asp Phe Leu Ser Ala Gln Gln Val Gln Ala Pro Val Lys Leu Tyr Ser
            485             490             495

Asp Trp Leu Ser Val Gly His Val Asp Glu Phe Leu Ser Phe Val Pro
            500             505             510

Ala Pro Asp Arg Lys Gly Phe Arg Leu Leu Leu Ala Ser Pro Arg Ser
```

-continued

```
            515              520              525
Cys Tyr Lys Leu Phe Gln Glu Gln Gln Asn Glu Gly His Gly Glu Ala
    530              535              540
Leu Leu Phe Glu Gly Ile Lys Lys Lys Gln Gln Lys Ile Lys Asn
545              550              555              560
Ile Leu Ser Asn Lys Thr Leu Arg Glu His Asn Ser Phe Val Glu Arg
                565              570              575
Cys Ile Asp Trp Asn Arg Glu Leu Leu Lys Arg Glu Leu Gly Leu Ala
            580              585              590
Glu Ser Asp Ile Ile Asp Ile Pro Gln Leu Phe Lys Leu Lys Glu Phe
            595              600              605
Ser Lys Ala Glu Ala Phe Phe Pro Asn Met Val Asn Met Leu Val Leu
    610              615              620
Gly Lys His Leu Gly Ile Pro Lys Pro Phe Gly Pro Val Ile Asn Gly
625              630              635              640
Arg Cys Cys Leu Glu Glu Lys Val Cys Ser Leu Leu Glu Pro Leu Gly
            645              650              655
Leu Gln Cys Thr Phe Ile Asn Asp Phe Phe Thr Tyr His Ile Arg His
            660              665              670
Gly Glu Val His Cys Gly Thr Asn Val Arg Arg Lys Pro Phe Ser Phe
            675              680              685
Lys Trp Trp Asn Met Val Pro
    690              695
```

```
<210> SEQ ID NO 2
<211> LENGTH: 2109
<212> TYPE: DNA
<213> ORGANISM: Artificial Sequence
<220> FEATURE:
<223> OTHER INFORMATION: It is synthesized.

<400> SEQUENCE: 2
gaattcgccg ccaccatggg cgcttcctgg agccacccc agttcgagaa gggtggtggc     60
agcggtggcg gcagcggagg ttcagcttgg tcccaccctc agttcgaaaa gatggcccag    120
ggtactctga tccgtgtcac ccccgagcag cctacccacg ccgtctgcgt gctgggtacc    180
ctgactcagc tggacatctg ctccagcgct cctgaggact gcacttcctt cagcatcaac    240
gcttcccctg gtgtcgtcgt ggacatcgcc cacggtcctc ccgccaagaa gaagtccacc    300
ggtagcagca cttggcctct ggaccctggt gtggaggtca ccctgactat gaaggtggct    360
tccggcagca ccgcgacca gaaggtccag atcagctact acggtcctaa gacccccccc    420
gtgaaggctc tgctgtacct gactggcgtc gagatcagcc tgtgcgctga catcacccgt    480
actggcaagg tgaagcctac ccgtgctgtg aaggaccagc gcacttggac ctggggccct    540
tgcggtcagg gtgctatcct gctggtcaac tgcgaccgtg acaacctgga gtcctccgct    600
atggactgcg aagacgacga agtgctggac agcgaggacc tgcaggacat gtccctgatg    660
actctgagca ctaagactcc caaggacttc ttcaccaacc acaccctggt cctgcacgtc    720
gcccgcagcg agatggacaa ggtgcgcgtc ttccaggcta cccgcggtaa actgtcctcc    780
aagtgcagcg tcgtgctggg ccctaagtgg ccttcccact acctgatggt ccccggtggt    840
aaacacaaca tggacttcta cgtcgaggcc ctggccttcc ctgacactga cttccctggt    900
ctgatcactc tgaccatctc cctgctggac actagcaacc tggaactgcc cgaggccgtg    960
gtgttccagg acagcgtcgt gttccgtgtg gctccctgga tcatgacccc caacacccag   1020
```

-continued

```
ccccctcagg aagtgtacgc ttgcagcatc ttcgaaaacg aggacttcct gaagagcgtc   1080
actaccctgg ctatgaaggc caagtgcaag ctgaccatct gccctgagga agagaacatg   1140
gacgaccagt ggatgcagga cgaaatggag atcggctaca tccaggctcc tcacaagact   1200
ctgcccgtcg tgttcgacag cccccgtaac cgcggtctga aggaatttcc catcaagcgc   1260
gtgatgggcc ctgacttcgg ttacgtgacc cgtggtcccc agactggcgg tatctccggc   1320
ctggacagct cggcaacct ggaggtctcc cccctgtga ctgtgcgcgg caaggagtac    1380
cccctgggtc gcatcctgtt cggcgactcc tgctaccctt ccaacgactc ccgtcagatg   1440
caccaggctc tgcaggactt cctgagcgcc cagcaggtgc aggctcctgt gaagctgtac   1500
agcgactggc tgagcgtcgg tcacgtcgac gagttcctgt ccttcgtgcc tgccctgac    1560 cgcaagggct tccgcctgct gctggccagc cccagatcct gctacaagct gttccaggag   1620
cagcagaacg aaggccacgg tgaggctctg ctgttcgaag gcatcaagaa gaagaagcag   1680
cagaagatca agaacatcct gagcaacaag actctgcgcg aacacaactc cttcgtcgaa   1740
cgttgcatcg actggaaccg tgaactgctg aagcgcgagc tgggcctggc cgagagcgac   1800
atcatcgaca tccctcagct gttcaagctg aaggaatttt ctaaggccga agcctttttc   1860
cctaacatgg tgaacatgct ggtgctgggt aaacacctgg gtatccctaa gcccttcggt   1920
cccgtcatca acggccgctg ctgcctggag gagaaggtct gctccctgct ggagcccctg   1980
ggtctgcagt gcaccttcat caacgacttc ttcacttacc acatccgtca cggcgaagtg   2040
cactgcggta ccaacgtgcg ccgcaagcct ttctccttca gtggtggaa catggtgcct   2100 taaaagctt                                                           2109
```

<210> SEQ ID NO 3
<211> LENGTH: 469
<212> TYPE: PRT
<213> ORGANISM: Artificial Sequence
<220> FEATURE:
<223> OTHER INFORMATION: It is synthesized.

<400> SEQUENCE: 3

```
Met Lys His Leu Trp Phe Phe Leu Leu Leu Val Ala Ala Pro Arg Trp
1               5                   10                  15

Val Leu Ser Glu Val Lys Leu Gln Glu Ser Gly Pro Gly Ile Leu Gln
            20                  25                  30

Pro Ser Gln Thr Leu Ser Leu Thr Cys Ser Phe Ser Gly Phe Ser Leu
        35                  40                  45

Ser Thr Ser Gly Met Cys Val Gly Trp Ile Arg Gln Pro Ser Gly Lys
    50                  55                  60

Gly Leu Glu Trp Leu Ala His Ile Trp Trp Asp Asp Asp Lys Arg Tyr
65                  70                  75                  80

Asn Pro Ala Leu Lys Ser Arg Leu Thr Ile Ser Lys Asp Thr Ser Ser
                85                  90                  95

Asn Gln Val Phe Leu Lys Ile Ala Ser Val Asp Thr Ala Asp Thr Ala
            100                 105                 110

Thr Tyr Tyr Cys Ala Arg Tyr Tyr Arg Phe Asp Glu Gly Phe Asp Tyr
        115                 120                 125

Trp Gly Gln Gly Thr Thr Leu Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
```

```
               165              170              175
Thr Val Ser Trp Asn Ser Gly Ala Leu Thr Ser Gly Val His Thr Phe
            180              185              190
Pro Ala Val Leu Gln Ser Ser Gly Leu Tyr Ser Leu Ser Ser Val Val
            195              200              205
Thr Val Pro Ser Ser Ser Leu Gly Thr Gln Thr Tyr Ile Cys Asn Val
            210              215              220
Asn His Lys Pro Ser Asn Thr Lys Val Asp Lys Lys Val Glu Pro Lys
225              230              235              240
Ser Cys Asp Lys Thr His Thr Cys Pro Pro Cys Pro Ala Pro Glu Leu
            245              250              255
Leu Gly Gly Pro Ser Val Phe Leu Phe Pro Pro Lys Pro Lys Asp Thr
            260              265              270
Leu Met Ile Ser Arg Thr Pro Glu Val Thr Cys Val Val Val Asp Val
            275              280              285
Ser His Glu Asp Pro Glu Val Lys Phe Asn Trp Tyr Val Asp Gly Val
            290              295              300
Glu Val His Asn Ala Lys Thr Lys Pro Arg Glu Glu Gln Tyr Asn Ser
305              310              315              320
Thr Tyr Arg Val Val Ser Val Leu Thr Val Leu His Gln Asp Trp Leu
            325              330              335
Asn Gly Lys Glu Tyr Lys Cys Lys Val Ser Asn Lys Ala Leu Pro Ala
            340              345              350
Pro Ile Glu Lys Thr Ile Ser Lys Ala Lys Gly Gln Pro Arg Glu Pro
            355              360              365
Gln Val Tyr Thr Leu Pro Pro Ser Arg Glu Glu Met Thr Lys Asn Gln
            370              375              380
Val Ser Leu Thr Cys Leu Val Lys Gly Phe Tyr Pro Ser Asp Ile Ala
385              390              395              400
Val Glu Trp Glu Ser Asn Gly Gln Pro Glu Asn Asn Tyr Lys Thr Thr
            405              410              415
Pro Pro Val Leu Asp Ser Asp Gly Ser Phe Phe Leu Tyr Ser Lys Leu
            420              425              430
Thr Val Asp Lys Ser Arg Trp Gln Gln Gly Asn Val Phe Ser Cys Ser
            435              440              445
Val Met His Glu Ala Leu His Asn His Tyr Thr Gln Lys Ser Leu Ser
            450              455              460
Leu Ser Pro Gly Lys
465
```

```
<210> SEQ ID NO 4
<211> LENGTH: 1419
<212> TYPE: DNA
<213> ORGANISM: Artificial Sequence
<220> FEATURE:
<223> OTHER INFORMATION: It is synthesized.

<400> SEQUENCE: 4
gccgccacca tgaagcacct gtggttcttt ctgctgctgg tggccgctcc tagatgggtg      60
ctgagcgagg tgaagctgca ggagtcagga cctgggatat tgcagccctc ccagaccctc     120
agtctgactt gttctttctc tgggtttca ctgagcactt ctggtatgtg tgtaggctgg      180
attcgtcagc cttcagggaa gggtctggag tggctggcac acatttggtg ggatgatgac     240
aagcgctata acccagccct taagagccga ctgacaatct ccaaggatac ctccagcaac     300
```

-continued

```
caggttttcc tcaagatcgc cagtgtggac actgcagata ctgccacata ctactgtgct    360
cgatactata ggttcgacga agggtttgac tactgggggcc aaggcaccac tctcacagtc    420
tcctcagcta gcaccaaggg accttctgtg ttccctctgg ctccttcttc taagtccact    480
tccggtggta cagcagctct gggttgtctg gtgaaggatt acttcccaga accagtgact    540
gtgtcctgga actccggagc tctgacttct ggagtgcata cttcccagc agtgctgcaa    600 tctagcggac tgtactctct gtcttccgtg gtgactgtgc cttcttcttc cctggggact    660
caaacttaca tctgcaacgt gaaccacaag ccctccaaca ccaaggtgga caagaaggtg    720
gagccaaaga gctgcgataa gacccacacc tgtccacctt gtccagctcc agaactgctg    780
ggtgggcctt ctgtgtttct gttcccacct aagccaaagg ataccctgat gatctctagg    840
accccagaag tgacctgtgt ggtcgtcgat gtgtctcatg aagaccctga agtgaagttc    900
aactggtacg tggacggggt ggaagtgcat aacgcaaaga ccaagcccag ggaagagcaa    960
tacaactcca cctacagggt ggtctccgtc ctgacagtcc tgcatcagga ttggctgaac    1020
ggcaaggagt acaagtgcaa ggtctccaat aaagccctgc ctgcccctat cgagaaaacc    1080
attagcaaag ccaaaggcca gccccgggag ccccaggtct atacactgcc ccccagcagg    1140
gaggagatga caaaaaatca ggtcagcctg acatgcctgg tcaaaggctt ttatcccagc    1200
gacattgccg tcgagtggga gtccaatggc cagcccgaga taattataa aacaacaccc    1260 cccgtcctgg acagcgacgg cagctttttt ctgtatagca aactgacagt cgataaaagc    1320
aggtggcagc agggcaatgt cttttcctgc agcgtcatgc acgaggccct gcacaatcac    1380
tatactcaga aaagcctgag cctgtcccc gggaaatga                            1419
```

<210> SEQ ID NO 5
<211> LENGTH: 239
<212> TYPE: PRT
<213> ORGANISM: Artificial Sequence
<220> FEATURE:
<223> OTHER INFORMATION: It is synthesized.

<400> SEQUENCE: 5

```
Met Val Leu Gln Thr Gln Val Phe Ile Ser Leu Leu Trp Ile Ser
1               5                   10                  15

Gly Ala Tyr Gly Asp Ile Val Ile Thr Gln Asp Glu Leu Ser Asn Pro
                20                  25                  30

Val Thr Leu Gly Thr Ser Ala Ser Ile Ser Cys Arg Ser Ser Lys Ser
            35                  40                  45

Leu Leu His Ser Asp Gly Ile Thr Tyr Leu Tyr Trp Tyr Leu Gln Lys
        50                  55                  60

Pro Gly Gln Ser Pro Gln Leu Leu Ile Tyr Gln Met Ser Asn Leu Ala
65                  70                  75                  80

Ser Gly Val Pro Asp Arg Phe Ser Ser Ser Gly Ser Gly Thr Asp Phe
                85                  90                  95

Thr Leu Arg Ile Ser Arg Val Glu Ala Glu Asp Val Gly Val Tyr Tyr
                100                 105                 110

Cys Ala Gln Asn Leu Glu Leu Pro Leu Thr Phe Gly Ala Gly Thr Lys
            115                 120                 125

Leu Glu Leu Lys Arg Thr Val Ala Ala Pro Ser Val Phe Ile Phe Pro
        130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
```

-continued

```
                        165                  170                  175
Asn Ala Leu Gln Ser Gly Asn Ser Gln Glu Ser Val Thr Glu Gln Asp
                180                  185                  190

Ser Lys Asp Ser Thr Tyr Ser Leu Ser Ser Thr Leu Thr Leu Ser Lys
            195                  200                  205

Ala Asp Tyr Glu Lys His Lys Val Tyr Ala Cys Glu Val Thr His Gln
        210                  215                  220

Gly Leu Ser Ser Pro Val Thr Lys Ser Phe Asn Arg Gly Glu Cys
225                  230                  235
```

<210> SEQ ID NO 6
<211> LENGTH: 729
<212> TYPE: DNA
<213> ORGANISM: Artificial Sequence
<220> FEATURE:
<223> OTHER INFORMATION: It is synthesized.

<400> SEQUENCE: 6

```
gccgccacca tggtgctgca gacccaggtg ttcatctctc tgctgctgtg gatctccggc      60
gcctacggcg atatcgtgat aacccaagat gaactctcca atccagtcac tcttggaaca     120
tcagcttcca tctcctgcag gtctagtaag agtctcctac atagtgatgg catcacttat     180
ttgtattggt atctgcagaa gccaggccag tctcctcagc tcctgattta tcagatgtcc     240
aaccttgcct caggagtccc agacaggttc agtagcagtg ggtcaggaac tgatttcaca     300
ctgagaatca gcagagtgga ggctgaggat gtgggtgttt attactgtgc tcaaaatcta     360
gaacttccgc tcacgttcgg tgctgggacc aagctggagc tgaaacgtac ggtggctgca     420
ccttctgtgt tcatcttccc tccatctgat gagcagctga agtctggaac cgcatctgtc     480
gtctgtctgc tgaacaactt ttaccccagg gaggctaagg tccaatggaa ggtggacaac     540
gccctgcagt ctggtaatag ccaggaaagc gtgaccgaac aggattccaa ggactccacc     600
tactccctgt cctccacact gacactgagc aaagccgact atgaaaagca caaagtgtat     660
gcctgcgagg tcactcatca gggcctgtcc agccccgtga ctaaaagctt taatagggggg     720 gagtgctga                                                             729
```

<210> SEQ ID NO 7
<211> LENGTH: 463
<212> TYPE: PRT
<213> ORGANISM: Artificial Sequence
<220> FEATURE:
<223> OTHER INFORMATION: It is synthesized.

<400> SEQUENCE: 7

```
Met Lys His Leu Trp Phe Phe Leu Leu Leu Val Ala Ala Pro Arg Trp
1               5                   10                  15

Val Leu Ser Glu Val Lys Leu Gln Glu Ser Gly Pro Ser Leu Val Ala
                20                  25                  30

Pro Ser Gln Asn Leu Ser Ile Thr Cys Thr Val Ser Gly Phe Ser Leu
            35                  40                  45

Thr Ser Tyr Ala Val His Trp Phe Arg Gln Pro Pro Gly Lys Gly Leu
        50                  55                  60

Glu Trp Leu Gly Val Ile Trp Ala Gly Gly Ser Thr Asn Cys Asn Ser
65                  70                  75                  80

Ala Leu Met Ser Arg Leu Ser Ile Ser Lys Asp Asn Ser Lys Ser Gln
                85                  90                  95

Val Phe Leu Lys Met Asn Ser Leu Gln Thr Asp Asp Thr Ala Met Tyr
```

-continued

```
                100             105              110
Tyr Cys Ala Arg Glu Ala Gly Ile Pro Phe Asp Tyr Trp Gly Gln Gly
        115             120             125

Thr Thr Leu Thr Val Ala Ser Thr Lys Gly Pro Ser Val Phe Pro Leu
    130             135             140

Ala Pro Ser Ser Lys Ser Thr Ser Gly Gly Thr Ala Ala Leu Gly Cys
145             150             155             160

Leu Val Lys Asp Tyr Phe Pro Glu Pro Val Thr Val Ser Trp Asn Ser
            165             170             175

Gly Ala Leu Thr Ser Gly Val His Thr Phe Pro Ala Val Leu Gln Ser
        180             185             190

Ser Gly Leu Tyr Ser Leu Ser Ser Val Val Thr Val Pro Ser Ser Ser
        195             200             205

Leu Gly Thr Gln Thr Tyr Ile Cys Asn Val Asn His Lys Pro Ser Asn
    210             215             220

Thr Lys Val Asp Lys Lys Val Glu Pro Lys Ser Cys Asp Lys Thr His
225             230             235             240

Thr Cys Pro Pro Cys Pro Ala Pro Glu Leu Leu Gly Gly Pro Ser Val
        245             250             255

Phe Leu Phe Pro Pro Lys Pro Lys Asp Thr Leu Met Ile Ser Arg Thr
        260             265             270

Pro Glu Val Thr Cys Val Val Val Asp Val Ser His Glu Asp Pro Glu
        275             280             285

Val Lys Phe Asn Trp Tyr Val Asp Gly Val Glu Val His Asn Ala Lys
    290             295             300

Thr Lys Pro Arg Glu Glu Gln Tyr Asn Ser Thr Tyr Arg Val Val Ser
305             310             315             320

Val Leu Thr Val Leu His Gln Asp Trp Leu Asn Gly Lys Glu Tyr Lys
        325             330             335

Cys Lys Val Ser Asn Lys Ala Leu Pro Ala Pro Ile Glu Lys Thr Ile
        340             345             350

Ser Lys Ala Lys Gly Gln Pro Arg Glu Pro Gln Val Tyr Thr Leu Pro
        355             360             365

Pro Ser Arg Glu Glu Met Thr Lys Asn Gln Val Ser Leu Thr Cys Leu
    370             375             380

Val Lys Gly Phe Tyr Pro Ser Asp Ile Ala Val Glu Trp Glu Ser Asn
385             390             395             400

Gly Gln Pro Glu Asn Asn Tyr Lys Thr Thr Pro Pro Val Leu Asp Ser
            405             410             415

Asp Gly Ser Phe Phe Leu Tyr Ser Lys Leu Thr Val Asp Lys Ser Arg
        420             425             430

Trp Gln Gln Gly Asn Val Phe Ser Cys Ser Val Met His Glu Ala Leu
        435             440             445

His Asn His Tyr Thr Gln Lys Ser Leu Ser Leu Ser Pro Gly Lys
    450             455             460
```

<210> SEQ ID NO 8
<211> LENGTH: 1401
<212> TYPE: DNA
<213> ORGANISM: Artificial Sequence
<220> FEATURE:
<223> OTHER INFORMATION: It is synthesized.

<400> SEQUENCE: 8
gccgccacca tgaagcacct gtggttcttt ctgctgctgg tggccgctcc tagatgggtg      60

-continued

```
ctgagcgagg tgaagctgca ggagtcagga cctagcctgg tggctccatc ccagaacctg      120
agcatcacct gcacagtgtc cggcttcagc ctgacctctt acgctgtgca ttggtttagg      180
cagccacctg gcaagggact ggagtggctg ggcgtgatct gggctggagg ctccacaaac      240
tgcaattctg ctctgatgtc ccggctgtct atctccaagg acaacagcaa gtctcaggtg      300
ttcctgaaga tgaactccct gcagaccgac gatacagcca tgtactattg tgcccgcgag      360
gctggcatcc catttgatta ttggggccag ggcaccacac tgaccgtggc tagcaccaag      420
ggaccttctg tgttccctct ggctccttct ctaagtcca cttccggtgg tacagcagct      480
ctgggttgtc tggtgaagga ttacttccca gaaccagtga ctgtgtcctg gaactccgga      540
gctctgactt ctggagtgca ctctttccca gcagtgctgc aatctagcgg actgtactct      600
ctgtcttccg tggtgactgt gccttcttct tccctgggga ctcaaactta catctgcaac      660
gtgaaccaca gccctccaa caccaaggtg gacaagaagg tggagccaaa gagctgcgat      720
aagacccaca cctgtccacc ttgtccagct ccagaactgc tgggtgggcc ttctgtgttt      780
ctgttcccac ctaagccaaa ggatacctg atgatctcta ggaccccaga agtgacctgt      840
gtggtcgtcg atgtgtctca tgaagaccct gaagtgaagt tcaactggta cgtggacggg      900
gtggaagtgc ataacgcaaa gaccaagccc agggaagagc aatacaactc cacctacagg      960
gtggtctccg tcctgacagt cctgcatcag gattggctga cggcaagga gtacaagtgc      1020 aaggtctcca ataaagccct gcctgcccct atcgagaaaa ccattagcaa agccaaaggc      1080
cagcccaggg agccccaggt ctatacactg ccccccagca gggaggagat gacaaaaaat      1140
caggtcagcc tgacatgcct ggtcaaaggc ttttatccca gcgacattgc cgtcgagtgg      1200
gagtccaatg gccagcccga gaataattat aaaacaacac ccccgtcct ggacagcgac      1260 ggcagctttt ttctgtatag caaactgaca gtcgataaaa gcaggtggca gcaggcaat      1320 gtcttttcct gcagcgtcat gcacgaggcc ctgcacaatc actatactca gaaaagcctg      1380
agcctgtccc ccgggaaatg a                                                1401
```

<210> SEQ ID NO 9
<211> LENGTH: 466
<212> TYPE: PRT
<213> ORGANISM: Artificial Sequence
<220> FEATURE:
<223> OTHER INFORMATION: It is synthesized.

<400> SEQUENCE: 9

```
Met Lys His Leu Trp Phe Phe Leu Leu Leu Val Ala Ala Pro Arg Trp
1               5                   10                  15

Val Leu Ser Glu Val Gln Leu Gln Glu Ser Gly Pro Glu Leu Glu Lys
            20                  25                  30

Pro Gly Ala Ser Val Lys Ile Ser Cys Lys Ala Ser Gly Tyr Ser Phe
        35                  40                  45

Thr Gly Tyr Asn Met Asn Trp Val Lys Gln Arg Asn Gly Lys Ser Leu
    50                  55                  60

Glu Trp Ile Gly Asn Ile Asp Pro Tyr Asn Gly Gly Thr Asn Tyr Asn
65                  70                  75                  80

Gln Lys Phe Lys Gly Lys Ala Thr Leu Ser Val Asp Lys Ser Ser Thr
                85                  90                  95

Thr Ala Tyr Met Gln Leu Lys Gly Leu Thr Ser Glu Asp Ser Ala Val
            100                 105                 110

Tyr Phe Cys Ala Arg Glu Thr Tyr Tyr Gly Asp Ala Met Asp Tyr Trp
```

```
            115               120               125

Gly Gln Gly Thr Ser Val Thr Val Ala Ser Thr Lys Gly Pro Ser Val
    130               135               140

Phe Pro Leu Ala Pro Ser Ser Lys Ser Thr Ser Gly Gly Thr Ala Ala
145               150               155               160

Leu Gly Cys Leu Val Lys Asp Tyr Phe Pro Glu Pro Val Thr Val Ser
                165               170               175

Trp Asn Ser Gly Ala Leu Thr Ser Gly Val His Thr Phe Pro Ala Val
                180               185               190

Leu Gln Ser Ser Gly Leu Tyr Ser Leu Ser Ser Val Val Thr Val Pro
                195               200               205

Ser Ser Ser Leu Gly Thr Gln Thr Tyr Ile Cys Asn Val Asn His Lys
    210               215               220

Pro Ser Asn Thr Lys Val Asp Lys Lys Val Glu Pro Lys Ser Cys Asp
225               230               235               240

Lys Thr His Thr Cys Pro Pro Cys Pro Ala Pro Glu Leu Leu Gly Gly
                245               250               255

Pro Ser Val Phe Leu Phe Pro Pro Lys Pro Lys Asp Thr Leu Met Ile
                260               265               270

Ser Arg Thr Pro Glu Val Thr Cys Val Val Val Asp Val Ser His Glu
    275               280               285

Asp Pro Glu Val Lys Phe Asn Trp Tyr Val Asp Gly Val Glu Val His
    290               295               300

Asn Ala Lys Thr Lys Pro Arg Glu Glu Gln Tyr Asn Ser Thr Tyr Arg
305               310               315               320

Val Val Ser Val Leu Thr Val Leu His Gln Asp Trp Leu Asn Gly Lys
                325               330               335

Glu Tyr Lys Cys Lys Val Ser Asn Lys Ala Leu Pro Ala Pro Ile Glu
                340               345               350

Lys Thr Ile Ser Lys Ala Lys Gly Gln Pro Arg Glu Pro Gln Val Tyr
                355               360               365

Thr Leu Pro Pro Ser Arg Glu Glu Met Thr Lys Asn Gln Val Ser Leu
    370               375               380

Thr Cys Leu Val Lys Gly Phe Tyr Pro Ser Asp Ile Ala Val Glu Trp
385               390               395               400

Glu Ser Asn Gly Gln Pro Glu Asn Asn Tyr Lys Thr Thr Pro Pro Val
                405               410               415

Leu Asp Ser Asp Gly Ser Phe Phe Leu Tyr Ser Lys Leu Thr Val Asp
                420               425               430

Lys Ser Arg Trp Gln Gln Gly Asn Val Phe Ser Cys Ser Val Met His
                435               440               445

Glu Ala Leu His Asn His Tyr Thr Gln Lys Ser Leu Ser Leu Ser Pro
    450               455               460

Gly Lys
465
```

```
<210> SEQ ID NO 10
<211> LENGTH: 1410
<212> TYPE: DNA
<213> ORGANISM: Artificial Sequence
<220> FEATURE:
<223> OTHER INFORMATION: It is synthesized.

<400> SEQUENCE: 10
gccgccacca tgaagcacct gtggttcttt ctgctgctgg tggccgctcc tagatgggtg      60
```

-continued

```
ctgagcgagg tgcagctgca ggagtcaggc cctgagctgg agaagcccgg cgctagcgtg       120
aagatcagct gcaaggcctc cggctactcc ttcaccggct acaatatgaa ttgggtgaag       180
cagagaaacg gcaagagcct ggagtggatc ggcaacatcg atccttacaa cggcggcaca       240
aattacaatc agaagttcaa gggcaaggcc accctgtccg tggataagag cagcacaacc       300
gcctacatgc agctgaaggg cctgacatcc gaggactccg ccgtgtactt ttgcgccagg       360
gagacctact acggcgacgc catggattac tggggccagg gcaccagcgt gacagtggct       420
agcaccaagg gaccttctgt gttccctctg gctccttctt ctaagtccac ttccggtggt       480
acagcagctc tgggttgtct ggtgaaggat tacttcccag aaccagtgac tgtgtcctgg       540
aactccggag ctctgacttc tggagtgcat actttcccag cagtgctgca atctagcgga       600
ctgtactctc tgtcttccgt ggtgactgtg ccttcttctt ccctgggac tcaaacttac       660 atctgcaacg tgaaccacaa gccctccaac accaaggtgg acaagaaggt ggagccaaag       720
agctgcgata gacccacac ctgtccacct tgtccagctc cagaactgct gggtgggcct       780
tctgtgtttc tgttcccacc taagccaaag gatacctga tgatctctag gaccccagaa       840
gtgacctgtg tggtcgtcga tgtgtctcat gaagaccctg aagtgaagtt caactggtac       900
gtggacgggg tggaagtgca taacgcaaag accaagccca gggaagagca atacaactcc       960
acctacaggt ggtctccgt cctgacagtc ctgcatcagg attggctgaa cggcaaggag      1020
tacaagtgca aggtctccaa taaagccctg cctgcccta tcgagaaaac cattagcaaa      1080
gccaaaggcc agcccaggga gccccaggtc tatacactgc cccccagcag ggaggagatg      1140
acaaaaaatc aggtcagcct gacatgcctg gtcaaaggct tttatcccag cgacattgcc      1200
gtcgagtggg agtccaatgg ccagcccgag aataattata aaacaacacc ccccgtcctg      1260
gacagcgacg gcagctttt tctgtatagc aaactgacag tcgataaaag caggtggcag      1320
cagggcaatg tcttttcctg cagcgtcatg cacgaggccc tgcacaatca ctatactcag      1380
aaaagcctga gcctgtcccc cgggaaatga                                     1410
```

<210> SEQ ID NO 11
<211> LENGTH: 238
<212> TYPE: PRT
<213> ORGANISM: Artificial Sequence
<220> FEATURE:
<223> OTHER INFORMATION: It is synthesized.

<400> SEQUENCE: 11

```
Met Val Leu Gln Thr Gln Val Phe Ile Ser Leu Leu Leu Trp Ile Ser
1               5                   10                  15

Gly Ala Tyr Gly Asp Ile Val Leu Thr Gln Ser Pro Ala Ser Leu Val
            20                  25                  30

Val Ser Leu Gly Gln Arg Ala Thr Ile Ser Cys Arg Ala Ser Glu Ser
        35                  40                  45

Val Asp Ser Tyr Gly Asn Ser Phe Met His Trp Tyr Gln Gln Lys Pro
    50                  55                  60

Gly Gln Pro Pro Lys Leu Leu Ile Tyr Arg Ala Ser Asn Leu Glu Ser
65                  70                  75                  80

Gly Ile Pro Ala Arg Phe Ser Gly Ser Gly Ser Arg Thr Asp Phe Thr
                85                  90                  95

Leu Thr Ile Asn Pro Val Glu Ala Asp Asp Val Ala Thr Tyr Tyr Cys
            100                 105                 110

Gln Gln Thr Asn Glu Asp Pro Phe Thr Phe Gly Ser Gly Thr Lys Leu
```

```
            115               120               125
Glu Ile Lys Arg Thr Val Ala Ala Pro Ser Val Phe Ile Phe Pro Pro
    130               135               140

Ser Asp Glu Gln Leu Lys Ser Gly Thr Ala Ser Val Val Cys Leu Leu
145               150               155               160

Asn Asn Phe Tyr Pro Arg Glu Ala Lys Val Gln Trp Lys Val Asp Asn
                165               170               175

Ala Leu Gln Ser Gly Asn Ser Gln Glu Ser Val Thr Glu Gln Asp Ser
            180               185               190

Lys Asp Ser Thr Tyr Ser Leu Ser Ser Thr Leu Thr Leu Ser Lys Ala
        195               200               205

Asp Tyr Glu Lys His Lys Val Tyr Ala Cys Glu Val Thr His Gln Gly
    210               215               220

Leu Ser Ser Pro Val Thr Lys Ser Phe Asn Arg Gly Glu Cys
225               230               235

<210> SEQ ID NO 12
<211> LENGTH: 726
<212> TYPE: DNA
<213> ORGANISM: Artificial Sequence
<220> FEATURE:
<223> OTHER INFORMATION: It is synthesized.

<400> SEQUENCE: 12
gccgccacca tggtgctgca gacccaggtg ttcatctctc tgctgctgtg gatctccggc      60
gcctacggcg acattgtgct gacccaatct ccagcttctt tggttgtgtc tctagggcag     120
agggccacca tatcctgcag agccagtgaa agtgttgata gttatggcaa tagttttatg     180
cactggtatc agcagaaacc aggacagcca cccaaactcc tcatctatcg tgcatccaac     240
ctagaatctg ggatccctgc caggttcagt ggcagtgggt ctaggacaga cttcaccctc     300
accattaatc ctgtggaggc tgatgatgtt gcaacctatt actgtcagca aactaatgag     360
gatccattca cgttcggctc ggggacaaag ttggaaataa aacgtacggt ggctgcacct     420
tctgtgttca tcttccctcc atctgatgag cagctgaagt ctggaaccgc atctgtcgtc     480
tgtctgctga caacttttta ccccagggag gctaaggtcc aatggaaggt ggacaacgcc     540
ctgcagtctg gtaatagcca ggaaagcgtg accgaacagg attccaagga ctccacctac     600
tccctgtcct ccacactgac actgagcaaa gccgactatg aaaagcacaa agtgtatgcc     660
tgcgaggtca ctcatcaggg cctgtccagc cccgtgacta aaagctttaa tagggggggag     720 tgctga                                                                726
```

ANTIGEN AND ANTIBODIES PREPARED BASED ON PADI4 SERVING AS TUMOR MARKER, AND APPLICATION THEREOF

CROSS REFERENCES

This application is the continuation of International Application No. PCT/CN2020/112240 filed on 28 Aug. 2020 which designated the U.S. and claims priority to Chinese Application No. CN202010669810.1 filed on 13 Jul. 2020, the entire contents of each of which are hereby incorporated by reference.

FIELD OF THE INVENTION

The present disclosure relates to an antigen and antibodies prepared based on peptidylarginine deiminase 4 (PADI4) serving as a tumor marker, and application thereof, and belongs to the technical field of molecular biological detection.

BACKGROUND OF THE INVENTION

Peptidylarginine deiminases (PADs or PADIs) are a family of enzymes that exist in human tissues. At present, five PADs (i.e. PAD1, 2, 3, 4, and 6) have been discovered. These enzymes are encoded by a cluster of genes located at human chromosome 1p36 and have different tissue distributions. PADs can perform post-translational modification on other tissue proteins in the presence of calcium ions. They can catalyze the conversion of an amino group of arginine in a polypeptide chain into a carbonyl group, thereby converting arginine into citrulline. Citrulline is a non-essential amino acid. The process of converting arginine in a polypeptide chain into citrulline under the catalysis of PADs is called citrullination. After a protein is citrullinated, its structure alters, resulting in alteration in its enzymatic activity, metabolic activity, regulatory functions, and structural functions. Therefore, as a protein post-translational modification manner, citrullination is as important as phosphorylation, acetylation, glycosylation, methylation, and ubiquitination.

Recently, through immunological, cell biochemical, and molecular genetic research, peptidylarginine deiminase 4 (PAD4 or PADI4) has been proven to play a key role in the pathogenesis of human rheumatoid arthritis, and moreover, it can be used as an adenocarcinoma marker and applied to the preparation of reagents for clinical diagnosis of adenocarcinoma. It is found from screening technologies such as tissue microarray that peptidylarginine deiminase 4 (PADI4) is significantly highly expressed in a variety of malignant tumor tissues and patients' blood (breast cancer, lung cancer, kidney cancer, bladder cancer, colon cancer, uterine cancer, ovarian cancer, etc.), and is lowly or not expressed in various benign tumors, chronic inflammations (gastric leiomyoma, uterine fibroid, cervical polyp, cholecystitis, cervicitis, synovitis, etc.), and healthy people. These results show that PADI4 is not only closely related to the pathogenesis of tumors, but also expressed in a variety of malignant tumor tissues, and thus, it is a broad-spectrum and detectable tumor marker.

Chinese patent CN101101290A (application No. 200610070392.4) discloses a tumor serum marker composed of peptidylarginine deiminase 4, and the tumor refers to one of breast cancer, liver cancer, kidney cancer, ovarian cancer, prostate cancer, and bladder cancer. The patent also discloses application of the tumor serum marker in the preparation of a reagent for clinical diagnosis of a tumor.

The reagent or kit for clinical diagnosis of a tumor prepared by the tumor serum maker of this disclosure can preliminarily determine whether a subject has a malignant tumor by detecting only one index, complete the health screening in a short detection time with low cost, and provide a reliable basis for clinical diagnosis. However, there is no kit for detecting PADI4 in a patient's serum at present in China. The main technical obstacle is that an antigen is a human protein PADI4, which is subjected to recombinant expression by using a baculovirus expression vector system, the N-terminus of the protein is added with a Twin Strep tag for purification, Sf9 cells are adopted, and it is necessary to obtain a soluble protein that serves as the antigen. Expression and purification tests find that PADI4 is expressed in Sf9 cells, the optimum expression conditions include: 30 ul of viral plasmids (M.O.I.-1) is used to infect Sf9 cells for 3 days, the technical obstacles are that after the expression and purification, the yield is low and only 0.34 mg/L, and the purification is only 80%, the preparation of a monoclonal antibody requires at least 3.5 mg of antigens, and therefore, it is necessary to enlarge the volume to obtain enough antigens. Meanwhile, the preparation of the antibody requires immunization, fusion, subcloning, screening, and stain stabilization, in the antibody production stage, because the protein PADI4 has high homology with a protein PADI2, the removal of a cross reaction during screening is also a main challenge obstructing the development of this technology.

Therefore, the development of a PADI4 detection kit that has high sensitivity and specificity, and stability and is used to detect PADI4 in a tumor serum of breast cancer, lung cancer, kidney cancer, bladder cancer, colon cancer, uterine cancer, ovarian cancer, or the like is of great significance for the screening, diagnosis, and treatment of the above-mentioned tumors.

SUMMARY OF THE INVENTION

In view of the defects in the prior art, the present disclosure provides application of peptidylarginine deiminase 4 (PADI4) in the preparation of a kit for diagnosing a tumor. The kit has high repeatability and stability, a broad spectrum, and detectability, and can be used for clinical diagnosis of a tumor.

In order to achieve the above-mentioned objective, the present disclosure adopts the following technical solutions.

An antigen is prepared based on peptidylarginine deiminase 4 serving as a tumor marker, and has an amino acid sequence shown as SEQ ID NO. 1.

Expressed genes of the above-mentioned antigen have a nucleotide sequence shown as SEQ ID NO. 2.

An antibody 135-B9 is prepared based on peptidylarginine deiminase 4 serving a tumor marker, and is composed of one heavy chain having an amino acid sequence shown as SEQ ID NO. 3 and one light chain having an amino acid sequence shown as SEQ ID NO. 5.

Expressed genes of the above-mentioned antibody 135-B9 have a heavy chain nucleotide sequence shown as SEQ ID NO. 4 and a light chain nucleotide sequence shown as SEQ ID NO. 6.

An antibody 197-A5 is prepared based on peptidylarginine deiminase 4 serving a tumor marker, and is composed of two heavy chains having amino acid sequences respectively shown as SEQ ID NO. 7 and SEQ ID NO. 9 and one light chain having an amino acid sequence shown as SEQ ID NO. 11.

Expressed genes of the above-mentioned antibody 197-A5 have heavy chain nucleotide sequences respectively shown as SEQ ID NO. 8 and SEQ ID NO. 10 and a light chain nucleotide sequence shown as SEQ ID NO. 12.

The above-mentioned antibody 135-B9 and antibody 197-A5 that serve as active ingredients are applied to the preparation of a reagent for detecting a tumor.

A kit for diagnosing a tumor includes:

an enzyme-linked immunosorbent assay (ELISA) plate coated with protein PADI4 monoclonal antibodies, control samples, a washing solution, a stop solution, a diluent, horseradish peroxidase-labeled streptavidin (HRP-SA), and a horseradish peroxidase chromogenic substrate;

wherein the protein PADI4 monoclonal antibodies include an antibody 135-B9 and an antibody 197-A5.

According to the present disclosure, preferably, the ELISA plate is a 96-well ELISA plate.

According to the present disclosure, preferably, the control samples include a positive control sample that is an artificially synthesized protein PADI4.

According to the present disclosure, preferably, the diluent is 5% FBS-PBST prepared by adding 10 mL of fetal bovine serum (FBS) into 90 mL of PBST solution and uniformly mixing the two.

According to the present disclosure, preferably, the washing solution is a PBST solution prepared by adding Tween-20 into a PBS solution with a pH value of 7.4 according to a volume percentage of 0.1% and uniformly mixing the two.

According to the present disclosure, preferably, the stop solution is 2 mol/L of hydrochloric acid solution.

According to the present disclosure, preferably, the horseradish peroxidase chromogenic substrate includes a chromogenic solution A and a chromogenic solution B, the chromogenic solution A is prepared by diluting hydrogen peroxide at a mass concentration of 30% by 1,000 multiples with a citrate buffer solution, and the chromogenic solution B is prepared by adding tetramethyl benzidine into a citrate buffer solution containing dimethyl sulfoxide at a mass concentration of 20% according a proportion of 0.4 mg/mL.

According to the present disclosure, preferably, the antibody 135-B9 is coated onto the ELISA plate, and the antibody 197-A5 is a biotin-labeled antibody 197-A5.

A preparation method of the above-mentioned kit for diagnosing a tumor includes the following steps:

(1) preparing an antigen having an amino acid sequence shown as SEQ ID NO. 1;

(2) preparing an antibody 135-B9 that is composed of one heavy chain having an amino acid sequence shown as SEQ ID NO. 3 and one light chain having an amino acid sequence shown as SEQ ID NO. 5;

(3) preparing an antibody 197-A5, labeling same with biotin to prepare a biotin-labeled antibody 197-A5, the antibody 197-A5 being composed of two heavy chains having amino acid sequences respectively shown as SEQ ID NO. 7 and SEQ ID NO. 9 and one light chain having an amino acid sequence shown as SEQ ID NO. 11; and (4) coating the antibody 135-B9 prepared at step (2) onto an ELISA plate, and assembling a kit to prepare the kit for diagnosing a tumor.

According to the present disclosure, preferably, the labeling at step (3) includes the following specific steps:

1) dissolving biotin into N,N-dimethylformamide (DMF) to prepare a biotin solution at a concentration of 20 mg/ml;

2) dissolving the antibody 197-A5 into PBS, and regulating a pH value to 8.5 with a carbonate buffer solution (CBS) to prepare an antibody 197-A5 solution at a concentration of 1 to 10 mg/mL;

3) mixing the biotin solution prepared at step 1) with the antibody 197-A5 solution prepared at step 2) according to a proportion of 5 μL of biotin solution per mg of antibody, and stirring the two for 2 h at room temperature in the dark; and 4) collecting a liquid (a mixture of the antibody buffer solution and the biotin buffer solution), dialyzing the liquid with PBS, and replacing PBS for 3 to 4 times during the dialysis.

According to the present disclosure, preferably, the coating at step (4) includes the following specific steps:

diluting the monoclonal antibody 135-B9 prepared at the previous step to 4 μg/mL with PBS with a pH value of 9.6 by a direct adsorption method, adding the diluted monoclonal antibody 135-B9 into a 96-well ELISA plate according to an addition amount of 100 μL/well, placing the ELISA plate at 37° C. for 2 h, washing with a washing solution, and spin-drying to prepare a 96-well ELISA plate coated with the monoclonal antibody 135-B9.

Introduction of Principles

As a tumor marker, PADI4 has broad-spectrum recognition. The existing markers can recognize at most 2 to 3 types of tumors. PADI4 and its product, i.e. citrullinated antithrombin, are significantly expressed in blood of patients suffering from breast cancer, lung cancer, kidney cancer, bladder cancer, colon cancer, uterine cancer, ovarian cancer, etc. The detection technology using PADI4 as a marker has low cost and can be applied to the health screening and outpatient preliminary detection of tumors. As a tumor marker, PADI4 has a clear mechanism of action and can provide a theoretical basis for determining the progress of tumor treatment. Most of the existing tumor markers do not have a clear mechanism of action, so they cannot be used to monitor the effect of tumor treatment. PADI4 can stimulate capillary proliferation of a tumor and inhibit apoptosis by modifying antithrombin, cytokeratin, and cellular fibronectin. Tests found that highly expressed PADI4 can interfere with regulation of downstream genes by a tumor suppressor gene P53. Therefore, the kit using PADI4 as a marker of the present disclosure has a board spectrum and specificity in clinical detection.

Beneficial Effects

The present disclosure performs immunization by using a specific antigen to obtain an antibody 135-B9 and an antibody 197-A5, and prepares a biotin-Avidin-ELISA kit by means of high magnification between biotin and horseradish peroxidase-labeled streptavidin on the basis of the conventional ELISA to detect a protein PADI4 expression level of a sample to be detected. The PADI4 detection kit of the present disclosure can effectively and stably detect an oncoprotein PADI4 level of a human serum, and has high specificity and test repeatability.

DETAILED DESCRIPTION OF THE EMBODIMENTS

Figure 1:
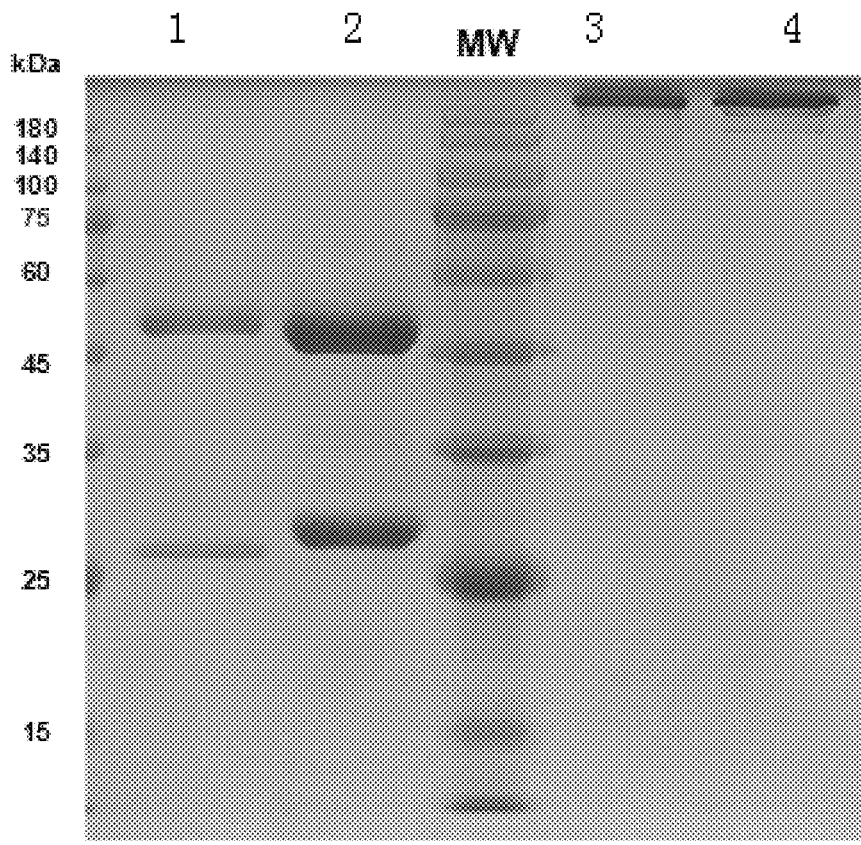
FIG. 1 is a denaturing and non-denaturing PAGE diagram of purified oncoprotein monoclonal antibodies 135-B9 and 197-A5.

The technical solutions of the present disclosure will be further described below with reference to the embodiments and drawings, but the scope of protection of the present disclosure is not limited thereto.

Sources of Reagents 96-well ELISA plates with item No. 3599 were purchased from Corning;

antigen proteins PADI4 were artificially synthesized;

health human serums were obtained from the health examination people of Shandong Cancer Hospital;

horseradish peroxidase-streptavidin with item No. 016-030-084 was purchased from Jackson;

washing solutions and stop solutions were purchased from AtaGenix; and horseradish peroxidase chromogenic substrates were TMB chromogenic solutions and purchased from Ata-Genix.

Example 1

Preparation of a Protein PADI4 Monoclonal Antibody (1) Preparation of an Antigen a) Codon Optimization and Gene Synthesis;

the protein PADI4 contains a total of 663 amino acids (AAs), has a molecular weight of 74.47 KDa, does not have a signal peptide and transmembrane helix, and has a high hydrophobicity region at 265-271 AAs. It is found from results of comprehensive homology comparison that a soluble protein is required to serve as an antigen. 1-260 AAs (a hydrophobic region is removed, and the homology is low) of a soluble protein PADI4 expressed in an *Escherichia coli* system was used to immunize mice to prepare a monoclonal antibody. A vector was pET28b, the C-terminus was bound to a 6 His tag on the vector, and a restriction site was NcoI/XhoI.

b) Plasmid Extraction (a Kit: Endo-Free Plasmid Mini Kit I (50), OMEGA Bio-Tek):

1) 4 mL of overnight cultured bacteria solution was taken and centrifuged at 12,000 rpm for 1 min, and thallus were collected;

2) 250 µL of Solution I was added to resuspend cells;

3) 250 µL of Solution II was added, and the thallus were completely lysed by means of gentle up-down reversal for 4 to 6 times and placed at room temperature for 2 min;

4) 350 µL of Solution III was added, and the mixture was immediately uniformly mixed by means of up-down reversal for several times until white flocculent precipitates appeared and centrifuged at 12,000 rpm for 10 min;

5) the supernate collected at the previous step was transferred into an adsorption column and centrifuged at 12,000 rpm for 1 min, and a waste liquid in a collection tube was removed;

6) 500 µL of Buffer HB was added into the adsorption column, the mixture was centrifuged at 12,000 rpm for 1 min, and a waste liquid in the collection tube was removed;

7) 700 µL of DNA Wash Buffer was added into the adsorption column, the mixture was centrifuged at 12,000 rpm for 1 min, a waste liquid was removed, and the mixture was washed again;

8) the empty column was centrifuged at 12,000 rpm for 2 min; and 9) the adsorption column was placed into an aseptic centrifuge tube, 50 µL of aseptic water was added, the centrifuge tube was placed at room temperature for 2 min and centrifuged at 12,000 rpm for 1 min, and a plasmid solution was collected into a new centrifuge tube and subjected to the previous processing again.

c) Transformation of DH10Bac by Plasmids

1) DH10Bac competent cells (purchased from Invitrogen) were defrosted on ices;

2) 100 uL of efficient DH10Bac competent cells was poured into a pre-cooled 1.5 mL tube;

3) 3 µL of plasmid DAN prepared at step b) was added to the cells, and the mixture was mixed gently;

4) the cells were incubated on ices for 30 min;

5) the cells were subjected to heat shock at 42° C. for 90 s;

6) the cells were placed on ices immediately for 2 min;

7) 900 µL of nonreactive LB medium was added;

8) the cells were subjected to shake culture at 180 rpm at 37° C. for 4 h;

9) 10 μL, 20 μL, and 30 μL of cells were respectively taken and coated onto LB plates according to different concentrations, three LB plates were coated for each concentration, and each of the LB plates contained 50 μg/mL of Kan, 7 μg/mL of Gentamicin, 10 μg/mL of tetracycline, 100 μg/mL of X-gal, and 40 μg/mL of IPTG; and 10) the cells were placed into an incubator and cultured in the dark at 37° C. for 48 h;

d) Blue-White Screening and Verification 1) the white clones cultured at step c) were picked up, streaked onto a new LB plate (containing 50 μg/mL of Kan, 7 μg/mL of Gentamicin, 10 μg/mL of tetracycline, 100 μg/mL of X-gal, and 40 μg/mL of IPTG), and cultured in the dark at 37° C. for 48 h;

2) 16 clones with white spots were respectively inoculated into 5 mL of solution containing 50 μg/mL of Kan, 7 μg/mL of Gentamici, and 10 μg/mL of tetracycline, and cultured at 200 rpm at 37° C. overnight;

3) recombinant Bacmid was verified by PCR, and the No. 1 to No. 16 monoclonal strains were verified;

4) recombinant plasmid DNA of a positive clone identified by PCR was extracted by using a kit (Endo-free plasmid Mini Kit I (50), OMEGA bio-tek);

e) Preparation of the P1 Generation of Recombinant Baculovirus (the Transfection of Sf9 Cells was Performed on a 6-Well Plate)

Figure 2:
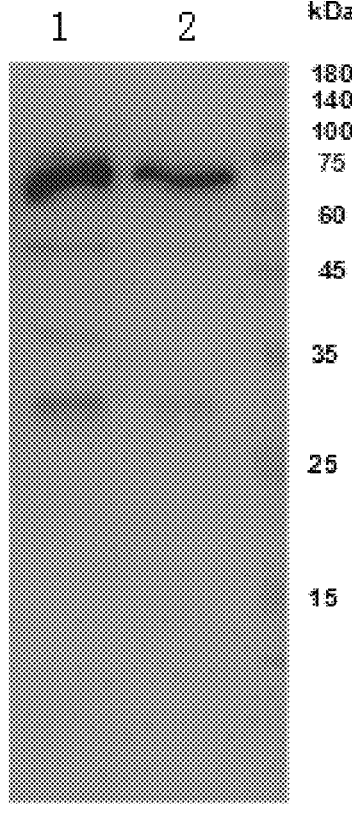
FIG. 2 is a diagram of analysis results of SDS-PAGE and Western blot of recognizing an antigen by the oncoprotein monoclonal antibody 135-B9.

1) $9 \times 10^5$ Sf9 cells were inoculated onto a 6-well plate, each well contained 2 mL of SFX medium containing an antibiotic, and the cells were cultured at 27° C. for 1 h;

2) preparation of transfection reagents: 2 μg of purified recombinant plasmid DNA was added into 100 μL of SFX medium without an antibiotic; a Cellfectin reagent was mixed uniformly and completely by means of up-down reversal for 5 to 10 times; 6 μL of Cellfectin reagent was sucked and added into 100 μL of SFX medium without an antibiotic; the Cellfectin reagent was added into the medium (with a total volume of about 210 μL) containing the plasmid DNA; and the mixture was gently mixed at room temperature for 3 min and incubated at room temperature for 15 min;

3) during the incubation of the DNA/transfection reagent mixture, the medium was removed from the cells, the cells were washed with 2 mL of medium without an antibiotic and a serum, and the washing medium was removed;

4) 0.8 mL of medium without an antibiotic and a serum was added into each tube containing the mixture and gently mixed with the mixture, and the mixture was added into the wells containing the cells;

5) the cells were cultured at 27° C. for 5 h;

6) the culture solution was removed, and 5 mL of complete medium (containing 50 units/mL of penicillin, 50 μg/mL of streptomycin, and 5% of serum) was added to the cells;

7) the cells were cultured at 27° C. for 1 week and centrifuged at 1,000 rpm/min for 5 min, and a supernatant was taken as a P1 virus strain (culture medium);

f) P1 Generation Expression Detection 1) the cells obtained by centrifugation were added into 10 mL of PBS and subjected to ultrasonic treatment for a total of 3 min, with each ultrasonic time of 2 s and an interval of 2 s; the cells were centrifuged at 12,000 rpm for 2 min to separate a supernate (native) from precipitates (denatured), and the precipitates were dissolved into 8Murea+PBS;

2) 12 μL of collected virus supernate (culture medium), the supernate (native), and the precipitates (denatured) were respectively sampled and subjected to SDS-PAGE (12%, 80 v spacer gel, 20 min, 120 v spacer gel, 45 min) to verify the expression;

g) Preparation of the P2 Generation of the Virus 1) results of the P1 generation expression detection showed that the target protein was expressed, and the P2 generation of the virus was prepared;

2) 200 mL of the cells was prepared, and 200 μL of the P1 generation of the virus was added;

3) the cells were placed into a humid incubator and cultured at 27° C. for 1 week, and centrifuged at 500×g for 5 min, and the cells and fragments were removed, and a supernate was collected as the P2 generation of the virus;

h) MOI Measurement 1) 30 mL of cell supernate ($2 \times 10^5$ cells/mL) in good conditions was added into a 6-well plate;

2) 30 μL, 150 μL, and 300 uL of P2 generation of the virus solution were respectively added to the cells, the cells were cultured for 48 h and 72 h, respectively, and 1.5 mL of cells was sampled for the expression detection and identification;

3) the collected sample was subjected to ultrasonic treatment for a total of 3 min, with each ultrasonic time of 2 s and an interval of 2 s; the sample was centrifuged at 12,000 rpm for 2 min to separate a supernate (native) from precipitates (denatured), and the precipitates were dissolved into 8Murea+PBS; and 4) SDS-PGAE identification was performed similarly;

200 mL Purification Testing (1) according to a result of the MOI measurement, 30 μL of P2 generation of the virus was taken to infect the cells for 72 h, which was the condition of purification testing;

(2) 200 mL of cells were cultured until the cells grew in good conditions, after the density of the cells reached $3 \times 10^6$, 30 μL of P2 generation of the virus was added, the cells were cultured for 72 h, and a sample was collected;

(3) the sample was centrifuged at 12,000 rpm for 30 min, and a supernate was collected; and (4) purification: STREP-tag affinity purification was performed by using a Strep-tactin resin;

(5) Preparation of a monoclonal antibody:

1) animal immunization: the antigen prepared at the previous step was used to immunize mice for 4 times, before fusion, the immunity was impacted, and the fusion was performed for 1 to 2 times;

2) cell fusion and screening: mice with high serum immunity were selected for cell fusion, the fusion was performed for 1 to 2 times, 5 to 6 rounds of ELISA screening were performed for each fusion (a cross-reaction was detected), in the first round, monoclonal antibodies were obtained, a strain was established, ascites was produced, and the antibody were paired. If no paired antibodies were obtained, the second round of cell fusion was performed, a cell strain obtained in the second round of fusion was established, ascites was produced, and then the cell strain was paired with the cell strain obtained in the first round. Thus, two hybridoma cell strain capable of stably secreting protein PADI4 monoclonal antibodies were obtained, and they were respectively named hybridoma cell strain 135-A1-B9 and hybridoma cell strain 197-C11-A5;

3) ascites production and purification: the cultured hybridoma cells were injected into abdominal cavities of the mice, after 1 to 2 weeks, ascites was produced, and the ascites was purified by protein A/G to prepare the protein PADI4 monoclonal antibodies 135-B9 and 197-A5;

FIG. 1 is a denaturing and non-denaturing PAGE diagram of the purified oncoprotein monoclonal antibodies 135-B9 and 197-A5, in the figure, Lane 1 is an SDS-PAGE result of a heavy chain and a light chain of the monoclonal antibody 135-B9 after denaturation, Lane 2 is an SDS-PAGE analysis result of heavy chains and a light chain of the monoclonal antibody 197-A5 after denaturation, Lane 3 is an SDS-PAGE result of the monoclonal antibody 135-B9 before denaturation, and Lane 4 is an SDS-PAGE result of the monoclonal antibody 197-A5 before denaturation. FIG. 2 is a diagram of an analysis result of Western blot of recognizing the antigen by the monoclonal antibody 135-B9, in the figure, Lane 1 is an SDS-PAGE analysis result of recognizing 0.5 μg of antigen by the monoclonal antibody 135-B9, and Lane 2 is an SDS-PAGE analysis result of recognizing 0.25 μg of antigen by the monoclonal antibody 135-B9;

(1) testing of a potency of the purified antibody: a potency of the monoclonal antibody was tested by an indirect ELISA method, the antibody with a potency ratio of greater than 1:64,000 was determined to be eligible, otherwise, the cell strain corresponding to the antibody was cultured again, the cells were injected into mice, ascites was produced, and antibody was purified; and (2) the purified antibody was labeled (Biotin)

Biotin was dissolved into DMF until the concentration was 20 mg/mL;

ii) the antibody was dissolved into PBS, and a pH value was regulated to 8.5 with CBS until the final concentration was 1 to 10 mg/mL;

iii) every 1 mg of antibody was added with 5 μL of biotin solution, and the mixture was stirred in the dark at room temperature for 2 h; and iv) a reactant was collected and dialyzed with PBS overnight, and PBS was replaced for 3 to 4 times during dialysis.

Biotinylated monoclonal antibody 197-A5

1) Biotin was dissolved into DMF until the concentration was 20 mg/mL;

2) the antibody was dissolved into PBS, and a pH value was regulated to 8.5 with CBS until the final concentration was 1 to 10 mg/mL;

3) every 1 mg of antibody was added with 5 uL of biotin solution, and the mixture was stirred in the dark at room temperature for 2 h; and 4) a reactant was collected and dialyzed with PBS overnight, and PBS was replaced for 3 to 4 times during dialysis.

The above-mentioned components were assembled into a kit for diagnosing a tumor in a conventional manner.

Coating of 96-well ELISA plate:

the monoclonal antibody 135-B9 prepared at the previous step was diluted to 4 μg/mL with PBS with a pH value of 9.6 by a direct adsorption method, the diluted monoclonal antibody 135-B9 was added into a 96-well ELISA plate according to an addition amount of 100

μL/well, and the ELISA plate was placed at 37° C. for 2 h, washed with a washing solution, and spin-dried to prepare a 96-well ELISA plate coated with the monoclonal antibody 135-B9.

Example 2

Steps of using the kit of Example 1 were as follows:

1) the plate coated with the antibody was resuscitated and balanced at room temperature;

2) standard samples (PADI4) were diluted at seven gradients from 10 ng/mL to 0.015625 ng/mL with diluents, 100 μL of diluted sample was added into each well, the last well was a blank control and added with 100 μL of diluent, and the plate was placed at 37° C. for 1.5 h;

3) the plate was washed with 300 μL of PBST for 5 times, and was patted dry;

4) 197-C11-A5-Antibody-Bio was diluted to 2 ug/mL with a diluent, 100 μL of diluted 197-C11-A5-Antibody-Bio was added into each well, and the plate was placed at 37° C. for 1 h;

5) the plate was washed with 300 μL of PBST for 5 times, and was patted dry;

6) Streptavidin-HRP was diluted to 1:2,000 with a diluent, 100 μL of diluted Streptavidin-HRP was added into each well, and the plate was placed at 37° C. for 30 min;

7) the plate was washed with 300 uL of PBST for 5 times, and was patted dry;

8) 100 μL of TMB chromogenic substrate was added into each well, and a chromogenic reaction was performed at 37° C. for 10 min; and 9) 50 μL of 2M hydrochloric acid was added into each well to stop the reaction.

3. Test Results:

within 15 min after the stop solution was added, the optical density (OD) of each detection well was measured by using an ELISA analyzer at a wavelength of 450 nm, and a test standard for the kit is that: if OD of a serum to be measured is greater than a certain threshold, the sample is determined to be positive, otherwise, the sample is determined to be negative. Tests found that a coefficient of variation (CV) of the coated 96-well ELISA plate prepared in the present disclosure is less than 20%. Kits of the same batch and different batches were tested, and test results showed that CV of the kits of the same batch and different batches were all less than 20%, which indicates that the PADI4 detection kit of the present disclosure has high accuracy.

Example 3 Clinical Sample Test Using the PADI4 Detection Kit of the Present Disclosure Case 1: 112 cases with breast cancer, 86 postoperative cases with breast cancer, 77 cases with hepatocellular carcinoma, 24 postoperative cases with hepatocellular carcinoma, 64 cases with esophageal cancer, 24 postoperative cases with esophageal cancer, 94 cases with stomach cancer, 43 postoperative cases with stomach cancer, 21 cases with colon cancer, 15 postoperative cases with colon cancer, 19 cases with rectal cancer, 28 postoperative cases with rectal cancer, 21 cases with pancreatic cancer, 6 postoperative cases with pancreatic cancer, 29 cases with ovarian cancer, 11 postoperative cases with ovarian cancer, and 160 normal control cases of matched gender and age were tested, and results are shown in Table 1:

TABLE 1

Detection data of PADI4 levels of subjects with tumor,
postoperative subjects, and normal subjects

| Object | Number of Samples (cases) | Serum OD (X ± SD) (ng/mL) |
|---|---|---|
| Breast cancer | 112 | 0.4093 ± 0.0233 |
| After breast cancer surgery | 86 | 0.2552 ± 0.022 |
| Health | 42 | 0.1801 ± 0.0211 |
| Hepatocellular carcinoma | 77 | 0.318 ± 0.0281 |
| After hepatocellular carcinoma surgery | 24 | 0.212 ± 0.0222 |
| Health | 42 | 0.0979 ± 0.0155 |
| Esophageal cancer | 64 | 0.4444 ± 0.0289 |
| After esophageal cancer surgery | 24 | 0.2126 ± 0.0244 |
| Health | 44 | 0.2403 ± 0.0603 |
| Stomach cancer | 94 | 0.4189 ± 0.0287 |
| After stomach cancer surgery | 43 | 0.3641 ± 0.0565 |
| Health | 38 | 0.2512 ± 0.0233 |
| Colon cancer | 21 | 0.3417 ± 0.0292 |
| After colon cancer surgery | 15 | 0.1678 ± 0.0224 |
| Health | 17 | 0.1404 ± 0.0299 |
| Rectal cancer | 19 | 0.2632 ± 0.0377 |
| After rectal cancer surgery | 28 | 0.1997 ± 0.026 |
| Health | 17 | 0.2012 ± 0.0378 |
| Pancreatic cancer | 21 | 0.3769 ± 0.0565 |
| After pancreatic cancer surgery | 6 | 0.229 ± 0.0874 |
| Health | 60 | 0.2365 ± 0.0198 |
| Ovarian cancer | 29 | 0.5053 ± 0.0477 |
| After ovarian cancer surgery | 11 | 0.3941 ± 0.0351 |
| Health | 23 | 0.1488 ± 0.0148 |

All the test data were obtained from 3 repeated tests. The tests found that the PADI4 expression levels of the serums of the subjects with a variety of malignant tumors, such as breast cancer, hepatocellular carcinoma, esophageal cancer, stomach cancer, colorectal cancer, pancreatic cancer, and ovarian cancer, are higher than those of the serums of the health controls, and differences are statistically significant ($P<0.05$). The PADI4 expression levels of the serums of the postoperative subjects with breast cancer, hepatocellular carcinoma, stomach cancer, colorectal cancer, pancreatic cancer, ovarian cancer, etc. are significantly decreased.

Figure 3:
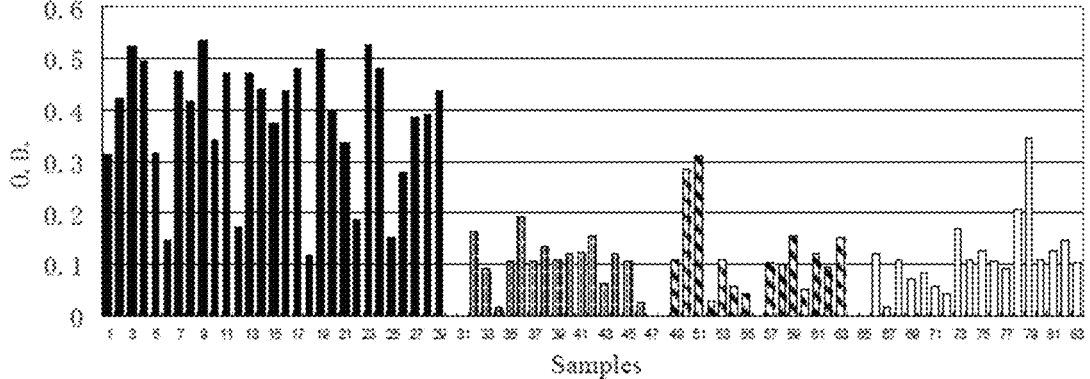
FIG. 3 is a diagram of PADI4 expression levels of absorption peaks of serums of subjects with breast cancer, postoperative subjects with breast cancer, subjects with breast fibroadenomas, and health subjects at 450 nm that are detected by an ELISA method.
Figure 4:
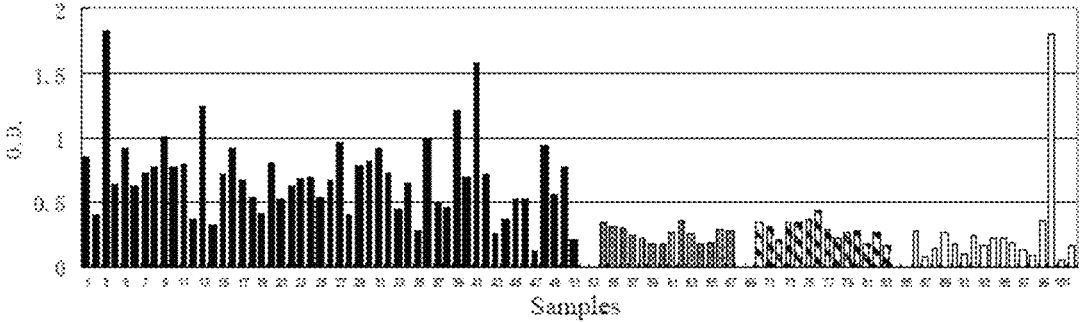
FIG. 4 is a diagram of PADI4 expression levels of absorption peaks of serums of subjects with liver cancer, postoperative subjects with liver cancer, subjects with cavernous liver hemangiomas, and health subjects at 450 nm that are detected by an ELISA method.
Figure 5:
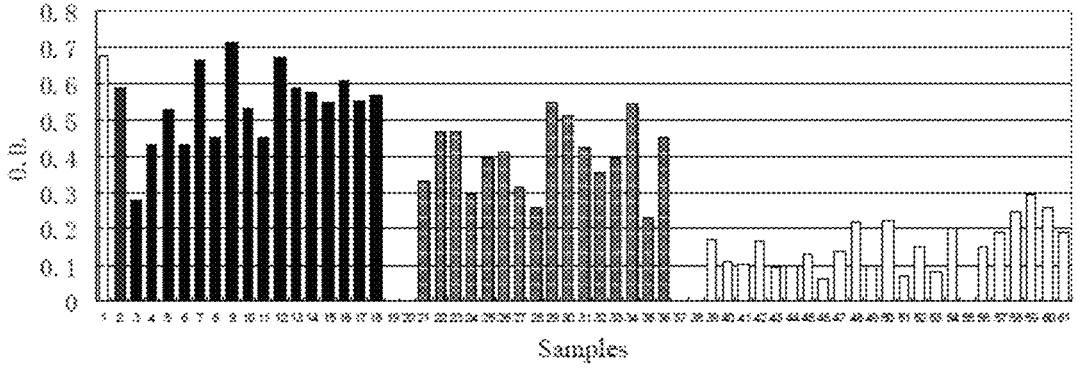
FIG. 5 is a diagram of PADI4 expression levels of absorption peaks of serums of subjects with ovarian cancer, postoperative subjects with ovarian cancer, and health subjects at 450 nm that are detected by an ELISA method.
Figure 6:
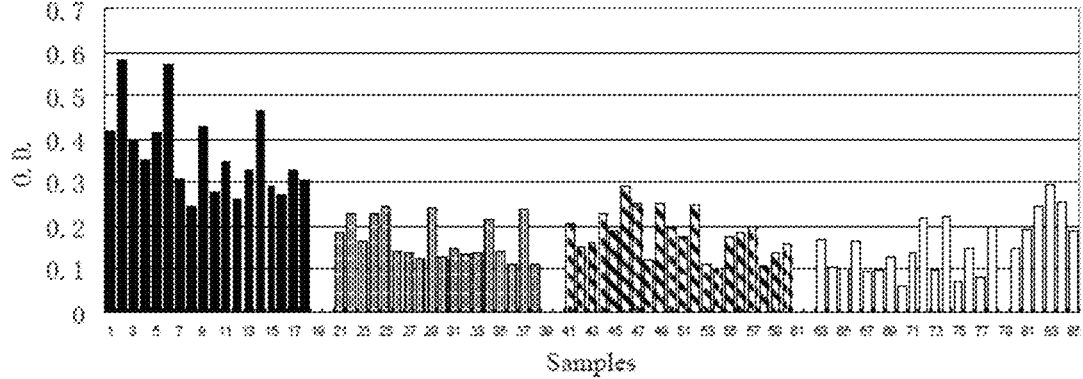
FIG. 6 is a diagram of PADI4 expression levels of absorption peaks of serums of subjects with prostate cancer, postoperative subjects with prostate cancer, subjects with benign prostate hyperplasia, and health subjects at 450 nm that are detected by an ELISA method.

Case 2: blood of the subjects with tumor was tested by an ELISA method, and it is found that PADI4 and its product, i.e. citrullinated antithrombin, are significantly expressed in the blood of the subjects with breast cancer, lung cancer, kidney cancer, bladder cancer, colon cancer, uterus cancer, ovarian cancer, etc., but are not or lowly expressed in the normal subjects. FIG. 3 is a diagram of the PADI4 expression levels of the serums of the subjects with a variety of tumors, the postoperative subjects, and the health subjects that are detected by the ELISA method. In the histogram, each column represents an absorption peak of the serum of the patient or health subject at 450 nm. The results show that compared with the serums of some subjects with benign tumor, postoperative subjects, and normal subjects, the PADI4 expression levels of the serums of the subjects with malignant tumors, such as breast cancer, liver cancer, kidney cancer, ovarian cancer, prostate cancer, bladder cancer, etc., are significantly increased.

Control 1

In order to further described the outstanding effect of the technical solutions obtained by the present disclosure in detecting a protein PADI4 expression level, other antibodies obtained by screening under the same conditions during the development process of the present disclosure were selected as effect controls of the antibodies of the present disclosure.

(1) Establishment of a double-antibody sandwich ELISA detection system: 26 monoclonal cell stains obtained by screening were used to produce antibodies, after purification, 21 strains of antibodies with high potency were selected for biotin labeling, a square titration experiment was performed, whether 26 strains of monoclonal antibodies can be paired with 18 strains of biotin-labeled antibodies was tested by a double-antibody sandwich ELISA method, the protein PADI4 was used as a standard protein, the protein PADI2 was used as a negative control, and 9 strains of capture antibodies and 9 strains of biotin-labeled antibodies were selected for the following endogenesis test.

(2) Endogenous sample detection using paired antibodies: a square titration experiment was performed, whether the screened 9 strains of monoclonal antibodies can be paired with the 9 strains of biotin-labeled antibodies was tested by the double-antibody sandwich ELISA method, these screened antibodies were used as capture antibodies and coated onto ELISA plates, the biotin-labeled antibodies were used as detection antibodies, the protein PADI4 was used as a standard protein, the protein PADI2 was used as a negative control protein, positive serums and negative serums provided by owners were used as endogenous samples and respectively subjected to pairwise coupling verification. Through a square titration experiment, the most responsive 10 groups of antibody pairs with the maximum P/N (as shown in Table 2) were selected for the following optimization experiment.

TABLE 2

P/N of positive samples to negative samples that
are tested by each group of antibody pair

| P/N | 1 Antibody 26 | 2 Antibody 28 | 3 Antibody 31 | 4 Antibody 65 | 5 Antibody 116 |
|---|---|---|---|---|---|
| Biotin-31 | 0.1 | 0.7 | 2.6 | 1.4 | -6.8 |
| Biotin-65 | 0.2 | 1.3 | -9.2 | 0.0 | -0.2 |
| Biotin-122 | -5.0 | 1.9 | -11.9 | -0.3 | -0.1 |
| Biotin-135 | 3.0 | 3.1 | 2.1 | 2.5 | 1.3 |
| Biotin-137 | -1.1 | -0.2 | 1.4 | 0.6 | 0.2 |
| Biotin-139 | 2.4 | 3.8 | 1.4 | 2.6 | 0.9 |
| Biotin-148 | 3.9 | 1.1 | 2.0 | 0.8 | 0.6 |
| Biotin-197 | -3.3 | -8.9 | 1.9 | 1.8 | 0.4 |
| Biotin-200 | 3.3 | 2.3 | 3.3 | 3.9 | 2.6 |

| P/N | 6 Antibody 122 | 7 Antibody 135 | 8 Antibody 197 | 9 Antibody 200 |
|---|---|---|---|---|
| Biotin-31 | 1.5 | 1.6 | 1.8 | 0.7 |
| Biotin-65 | 0.3 | 6.0 | 2.1 | 249.1 |
| Biotin-122 | 0.4 | 4.7 | 3.1 | 6.9 |
| Biotin-135 | 2.8 | 0.6 | 3.1 | 0.8 |
| Biotin-137 | 7.8 | 2.5 | 0.3 | 3.2 |
| Biotin-139 | 2.0 | 2.7 | 0.6 | 3.0 |
| Biotin-148 | 2.0 | 3.0 | 2.1 | 4.9 |
| Biotin-197 | 0.8 | 2.9 | 1.2 | 3.5 |
| Biotin-200 | 3.6 | 0.4 | 5.3 | 4.1 |

(3) Preliminary screening of optimal antibody pair: the 10 groups of antibody pairs (see Table 2) determined at the previous step were used to test the protein PADI2, the protein PADI4, the positive serums, and the negative serum that were subjected to gradient dilution, and results are shown below:

TABLE 3

OD of the negative control protein tested
by the 10 groups of antibody pairs

| Plate-1 PADI2 | 1 Antibody | 2 Antibody | 3 Antibody | 4 Antibody | 5 Antibody |
|---|---|---|---|---|---|
| | 135 | 135 | 135 | 135 | 135 |
| A | 0.04 | 0.05 | 0.04 | 0.03 | 0.04 |
| B | 0.03 | 0.03 | 0.03 | 0.03 | 0.05 |
| C | 0.03 | 0.03 | 0.03 | 0.02 | 0.05 |
| D | 0.03 | 0.03 | 0.03 | 0.03 | 0.05 |
| E | 0.04 | 0.03 | 0.03 | 0.03 | 0.05 |
| F | 0.05 | 0.03 | 0.03 | 0.03 | 0.05 |
| G | 0.03 | 0.03 | 0.03 | 0.03 | 0.05 |
| H | 0.03 | 0.04 | 0.04 | 0.03 | 0.06 |
| | Biotin-139 | Biotin-148 | Biotin-197 | Biotin-65 | Biotin-122 |

| Plate-1 PADI2 | 6 Antibody | 7 Antibody | 8 Antibody | 9 Antibody | 10 Antibody |
|---|---|---|---|---|---|
| | 135 | 197 | 197 | 200 | 200 |
| A | 0.06 | 0.06 | 0.06 | 0.32 | 0.30 |
| B | 0.03 | 0.05 | 0.05 | 0.30 | 0.30 |
| C | 0.03 | 0.05 | 0.06 | 0.29 | 0.30 |
| D | 0.03 | 0.05 | 0.05 | 0.33 | 0.28 |
| E | 0.03 | 0.05 | 0.05 | 0.29 | 0.29 |
| F | 0.03 | 0.05 | 0.06 | 0.27 | 0.27 |
| G | 0.03 | 0.05 | 0.06 | 0.27 | 0.25 |
| H | 0.04 | 0.06 | 0.06 | 0.26 | 0.21 |
| | Biotin-137 | Biotin-135 | Biotin-200 | Biotin-148 | Biotin-197 |

The data in Table 3 indicate that neither of the 10 groups of antibody pairs recognize the negative control protein PADI2, and there is no cross reaction.

TABLE 4

OD of the positive control protein tested
by the 10 groups of antibody pair

| Plate-2 PADI4 | 1 Antibody | 2 Antibody | 3 Antibody | 4 Antibody | 5 Antibody |
|---|---|---|---|---|---|
| | 135 | 135 | 135 | 135 | 135 |
| A | 4.12 | 4.15 | 4.32 | 2.4 | 3.17 |
| B | 3.85 | 3.92 | 3.86 | 1.43 | 1.96 |
| C | 2.49 | 2.77 | 2.83 | 0.65 | 0.86 |
| D | 1.66 | 1.97 | 1.79 | 0.39 | 0.48 |
| E | 1.10 | 1.19 | 1.19 | 0.19 | 0.27 |
| F | 0.65 | 0.67 | 0.65 | 0.11 | 0.16 |
| G | 0.38 | 0.39 | 0.37 | 0.06 | 0.10 |
| H | 0.04 | 0.04 | 0.04 | 0.03 | 0.04 |
| | Biotin-139 | Biotin-148 | Biotin-197 | Biotin-65 | Biotin-122 |

| Plate-2 PADI4 | 6 Antibody 135 | 7 Antibody 197 | 8 Antibody 197 | 9 Antibody 200 | 10 Antibody 200 |
|---|---|---|---|---|---|
| A | 4.23 | 4.13 | 4.26 | 3.843 | 3.93 |
| B | 3.21 | 3.95 | 3.95 | 3.62 | 2.93 |
| C | 2.98 | 3.53 | 3.08 | 2.53 | 2.06 |
| D | 1.89 | 2.47 | 2.58 | 1.41 | 1.05 |
| E | 1.12 | 1.69 | 1.58 | 0.81 | 0.70 |
| F | 0.57 | 0.92 | 0.85 | 0.47 | 0.44 |
| G | 0.34 | 0.46 | 0.54 | 0.32 | 0.37 |
| H | 0.02 | 0.04 | 0.04 | 0.18 | 0.17 |
| | Biotin-137 | Biotin-135 | Biotin-200 | Biotin-148 | Biotin-197 |

The data in Table 4 indicate that all the 10 groups of antibody pairs can recognize the positive control protein PADI4.

TABLE 5

OD of the positive serums and negative serums that
are tested by the 10 groups of antibody pair

| Plate-3 + Serum | 1 Antibody | 2 Antibody | 3 Antibody | 4 Antibody | 5 Antibody |
|---|---|---|---|---|---|
| | 135 | 135 | 135 | 135 | 135 |
| A | 1.11 | 1.24 | 1.63 | 0.24 | 0.43 |
| B | 1.33 | 1.34 | 1.37 | 0.26 | 0.41 |
| C | 1.09 | 1.24 | 1.19 | 0.23 | 0.38 |
| D | 0.79 | 0.81 | 0.84 | 0.18 | 0.28 |
| E | 0.54 | 0.58 | 0.62 | 0.13 | 0.20 |
| F | 0.31 | 0.31 | 0.35 | 0.09 | 0.14 |
| G | 0.19 | 0.18 | 0.22 | 0.06 | 0.12 |
| H | 0.04 | 0.04 | 0.04 | 0.03 | 0.06 |
| | Biotin-139 | Biotin-148 | Biotin-197 | Biotin-65 | Biotin-122 |

| Plate-3 + Serum | 6 Antibody | 7 Antibody | 8 Antibody | 9 Antibody | 10 Antibody |
|---|---|---|---|---|---|
| | 135 | 197 | 197 | 200 | 200 |
| A | 2.08 | 0.52 | 0.63 | 0.54 | 0.61 |
| B | 1.98 | 0.76 | 0.88 | 0.80 | 0.77 |
| C | 1.67 | 0.68 | 0.76 | 0.58 | 0.68 |
| D | 1.18 | 0.53 | 0.68 | 0.50 | 0.55 |
| E | 0.80 | 0.31 | 0.47 | 0.36 | 0.45 |
| F | 0.50 | 0.24 | 0.36 | 0.30 | 0.34 |
| G | 0.30 | 0.13 | 0.24 | 0.29 | 0.28 |
| H | 0.03 | 0.04 | 0.04 | 0.20 | 0.21 |
| | Biotin-137 | Biotin-135 | Biotin-200 | Biotin-148 | Biotin-197 |

| Plate-4 − Serum | 1 Antibody | 2 Antibody | 3 Antibody | 4 Antibody | 5 Antibody |
|---|---|---|---|---|---|
| | 135 | 135 | 135 | 135 | 135 |
| A | 0.34 | 0.45 | 0.37 | 0.06 | 0.09 |
| B | 0.34 | 0.45 | 0.35 | 0.06 | 0.10 |
| C | 0.30 | 0.39 | 0.32 | 0.08 | 0.11 |
| D | 0.19 | 0.29 | 0.20 | 0.06 | 0.10 |
| E | 0.12 | 0.20 | 0.13 | 0.05 | 0.07 |
| F | 0.09 | 0.13 | 0.10 | 0.05 | 0.09 |
| G | 0.08 | 0.08 | 0.08 | 0.04 | 0.07 |
| H | 0.06 | 0.05 | 0.04 | 0.04 | 0.06 |
| | Biotin-139 | Biotin-148 | Biotin-197 | Biotin-65 | Biotin-122 |

| Plate-4 − Serum | 6 Antibody | 7 Antibody | 8 Antibody | 9 Antibody | 10 Antibody |
|---|---|---|---|---|---|
| | 135 | 197 | 197 | 200 | 200 |
| A | 0.36 | 0.45 | 0.34 | 0.28 | 0.29 |
| B | 0.33 | 0.39 | 0.41 | 0.29 | 0.30 |
| C | 0.28 | 0.38 | 0.37 | 0.39 | 0.34 |
| D | 0.24 | 0.26 | 0.30 | 0.35 | 0.32 |
| E | 0.14 | 0.20 | 0.22 | 0.29 | 0.29 |
| F | 0.08 | 0.14 | 0.19 | 0.32 | 0.26 |
| G | 0.06 | 0.11 | 0.12 | 0.29 | 0.26 |
| H | 0.04 | 0.06 | 0.06 | 0.30 | 0.25 |
| | Biotin-137 | Biotin-135 | Biotin-200 | Biotin-148 | Biotin-197 |

According to the data in Table 5, 5 groups of antibody pairs (Columns 1, 2, 3, 5, and 6) with positive serum OD/negative serum OD of greater than 3 were selected for the following optimization of the capture antibody and detection antibodies: three concentration gradients (1/2/4 ug/mL) were set for the capture antibody 135, and three concentration gradients (0.5/1/2 ug/mL) were respectively set for the 5 detection antibodies to test the protein PADI4 (subjected to doubling dilution from 0.1 ug/mL to 0.0015625 ug/mL), the negative serums (dilution multiple: 1/2/4 multiples), and the positive serums (dilution multiple: 1/2/4 multiples), and arrangements are shown in Table 6:

TABLE 6

| Plate-1 | 1 | 2 | 3 | 4 | 5 | 6 |
|---|---|---|---|---|---|---|
| A | Antibody | Antibody | Antibody | Antibody | Antibody | Antibody |
| B | 135 | 135 | 135 | 135 | 135 | 135 |
| C | 2 ug/ml | 2 ug/ml | 2 ug/ml | 2 ug/ml | 2 ug/ml | 2 ug/ml |
| D | | | | | | |
| E | | | | | | |
| F | | | | | | |
| G | | | | | | |
| H | | | | | | |

| Plate-1 | 7 | 8 | 9 | 10 | 11 | 12 |
|---|---|---|---|---|---|---|
| A | Antibody | Antibody | Antibody | Antibody | Antibody | Antibody |
| B | 135 | 135 | 135 | 135 | 135 | 135 |
| C | 2 ug/ml | 2 ug/ml | 4 ug/ml | 4 ug/ml | 4 ug/ml | 4 ug/ml |
| D | | | | | | |
| E | | | | | | |
| F | | | | | | |
| G | | | | | | |
| H | | | | | | |

| Plate-2 | 1 | 2 | 3 | 4 | 5 | 6 | 7 | 8 |
|---|---|---|---|---|---|---|---|---|
| A | Antibody | Antibody | Antibody | Antibody | Antibody | Antibody | Antibody | Antibody |
| B | 135 | 135 | 135 | 135 | 135 | 135 | 135 | 135 |
| C | 2 ug/ml | 2 ug/ml | 2 ug/ml | 2 ug/ml | 4 ug/ml | 4 ug/ml | 4 ug/ml | 4 ug/ml |
| D | | | | | | | | |
| E | | | | | | | | |
| F | | | | | | | | |
| G | | | | | | | | |
| H | | | | | | | | |

| Plate-1 | 1 | 2 | 3 | 4 | 5 | 6 |
|---|---|---|---|---|---|---|
| A | PADI4 0.1 ug/ml | PADI4 0.1 ug/ml | + Serum 1:1 | + Serum 1:1 | PADI4 0.1 ug/ml | PADI4 0.1 ug/ml |
| B | PADI4 0.05 ug/ml | PADI4 0.05 ug/ml | + Serum 1:2 | + Serum 1:2 | PADI4 0.05 ug/ml | PADI4 0.05 ug/ml |
| C | PADI4 0.025 ug/ml | PADI4 0.025 ug/ml | + Serum 1:4 | + Serum 1:4 | PADI4 0.025 ug/ml | PADI4 0.025 ug/ml |
| D | PADI4 0.0125 ug/ml | PADI4 0.0125 ug/ml | PBS | PBS | PADI4 0.0125 ug/ml | PADI4 0.0125 ug/ml |
| E | PADI4 0.00625 ug/ml | PADI4 0.00625 ug/ml | − Serum 1:1 | − Serum 1:1 | PADI4 0.00625 ug/ml | PADI4 0.00625 ug/ml |
| F | PADI4 0.003125 ug/ml | PADI4 0.003125 ug/ml | − Serum 1:2 | − Serum 1:2 | PADI4 0.003125 ug/ml | PADI4 0.003125 ug/ml |
| G | PADI4 0.0015625 ug/ml | PADI4 0.0015625 ug/ml | − Serum 1:4 | − Serum 1:4 | PADI4 0.0015625 ug/ml | PADI4 0.0015625 ug/ml |
| H | PBS | PBS | PBS | PBS | PBS | PBS |

| Plate-1 | 7 | 8 | 9 | 10 | 11 | 12 |
|---|---|---|---|---|---|---|
| A | + Serum 1:1 | + Serum 1:1 | PADI4 0.1 ug/ml | PADI4 0.1 ug/ml | + Serum 1:1 | + Serum 1:1 |
| B | + Serum 1:2 | + Serum 1:2 | PADI4 0.05 ug/ml | PADI4 0.05 ug/ml | + Serum 1:2 | + Serum 1:2 |
| C | + Serum 1:4 | + Serum 1:4 | PADI4 0.025 ug/ml | PADI4 0.025 ug/ml | + Serum 1:4 | + Serum 1:4 |
| D | PBS | PBS | PADI4 0.0125 ug/ml | PADI4 0.0125 ug/ml | PBS | PBS |
| E | − Serum 1:1 | − Serum 1:1 | PADI4 0.00625 ug/ml | PADI4 0.00625 ug/ml | − Serum 1:1 | − Serum 1:1 |
| F | − Serum 1:2 | − Serum 1:2 | PADI4 0.003125 ug/ml | PADI4 0.003125 ug/ml | − Serum 1:2 | − Serum 1:2 |
| G | − Serum 1:4 | − Serum 1:4 | PADI4 0.0015625 ug/ml | PADI4 0.0015625 ug/ml | − Serum 1:4 | − Serum 1:4 |
| H | PBS | PBS | PBS | PBS | PBS | PBS |

| Plate-2 | 1 | 2 | 3 | 4 | 5 | 6 | 7 | 8 |
|---|---|---|---|---|---|---|---|---|
| A | PADI4 0.1 ug/ml | PADI4 0.1 ug/ml | + Serum 1:1 | + Serum 1:1 | PADI4 0.1 ug/ml | PADI4 0.1 ug/ml | + Serum 1:1 | + Serum 1:1 |
| B | PADI4 0.05 ug/ml | PADI4 0.05 ug/ml | + Serum 1:2 | + Serum 1:2 | PADI4 0.05 ug/ml | PADI4 0.05 ug/ml | + Serum 1:2 | + Serum 1:2 |
| C | PADI4 0.025 ug/ml | PADI4 0.025 ug/ml | + Serum 1:4 | + Serum 1:4 | PADI4 0.025 ug/ml | PADI4 0.025 ug/ml | + Serum 1:4 | + Serum 1:4 |
| D | PADI4 0.0125 ug/ml | PADI4 0.0125 ug/ml | PBS | PBS | PADI4 0.0125 ug/ml | PADI4 0.0125 ug/ml | PBS | PBS |

TABLE 6-continued

| | | | | | | | | |
|---|---|---|---|---|---|---|---|---|
| E | PADI4 0.00625 ug/ml | PADI4 0.00625 ug/ml | – Serum 1:1 | – Serum 1:1 | PADI4 0.00625 ug/ml | PADI4 0.00625 ug/ml | – Serum 1:1 | – Serum 1:1 |
| F | PADI4 0.003125 ug/ml | PADI4 0.003125 ug/ml | – Serum 1:2 | – Serum 1:2 | PADI4 0.003125 ug/ml | PADI4 0.003125 ug/ml | – Serum 1:2 | – Serum 1:2 |
| G | PADI4 0.0015625 ug/ml | PADI4 0.0015625 ug/ml | – Serum 1:4 | – Serum 1:4 | PADI4 0.0015625 ug/ml | PADI4 0.0015625 ug/ml | – Serum 1:4 | – Serum 1:4 |
| H | PBS | PBS | PBS | PBS | PBS | PBS | PBS | PBS |

| Plate-1 | 1 | 2 | 3 | 4 | 5 | 6 | 7 | 8 | 9 | 10 | 11 | 12 |
|---|---|---|---|---|---|---|---|---|---|---|---|---|
| A | | Biotin-139 2 ug/ml | | | | | Biotin-148 2 ug/ml | | | Biotin-197 0.5 ug/ml | | |
| B | | | | | | | | | | | | |
| C | | | | | | | | | | | | |
| D | | | | | | | | | | | | |
| E | | | | | | | | | | | | |
| F | | | | | | | | | | | | |
| G | | | | | | | | | | | | |
| H | | | | | | | | | | | | |

| Plate-2 | 1 | 2 | 3 | 4 | 5 | 6 | 7 | 8 |
|---|---|---|---|---|---|---|---|---|
| A | | Biotin-122 2 ug/ml | | | | Biotin-137 0.5 ug/ml | | |
| B | | | | | | | | |
| C | | | | | | | | |
| D | | | | | | | | |
| E | | | | | | | | |
| F | | | | | | | | |
| G | | | | | | | | |
| H | | | | | | | | |

Date are shown in Table 7 (boldface is data-standard curve of PADI4; Rows D, E, and F of Columns 3, 4, 7, and 8 are data of the negative serums (diluted by 1/2/4 multiples); the remaining non-boldface is data of the positive serums):

TABLE 7

| Plate-1 | 1 | 2 | 3 | 4 | 5 | 6 |
|---|---|---|---|---|---|---|
| A | 4.09 | 4.14 | 4.48 | 4.66 | 4.11 | 4.26 |
| B | 2.43 | 2.46 | 4.30 | 4.59 | 2.36 | 2.61 |
| C | 1.48 | 1.35 | 4.49 | 4.67 | 1.43 | 1.71 |
| D | 0.87 | 0.91 | 0.13 | 0.14 | 0.86 | 1.00 |
| E | 0.58 | 0.53 | 0.95 | 1.23 | 0.49 | 0.55 |
| F | 0.33 | 0.32 | 0.75 | 0.91 | 0.36 | 0.38 |
| G | 0.24 | 0.21 | 0.48 | 0.55 | 0.25 | 0.26 |
| H | 0.13 | 0.10 | 0.11 | 0.11 | 0.12 | 0.15 |

| Plate-1 | 7 | 8 | 9 | 10 | 11 | 12 |
|---|---|---|---|---|---|---|
| A | 4.70 | 4.72 | 3.97 | 4.47 | 4.66 | 4.47 |
| B | 5.00 | 4.64 | 2.35 | 2.85 | 4.59 | 4.90 |
| C | 4.50 | 4.61 | 1.29 | 1.54 | 4.49 | 4.55 |
| D | 0.14 | 0.15 | 0.71 | 0.67 | 0.11 | 0.10 |
| E | 1.22 | 1.05 | 0.40 | 0.39 | 1.04 | 0.77 |
| F | 0.99 | 0.83 | 0.26 | 0.25 | 0.75 | 0.63 |
| G | 0.65 | 0.56 | 0.18 | 0.17 | 0.50 | 0.47 |
| H | 0.14 | 0.12 | 0.10 | 0.09 | 0.10 | 0.09 |

| Plate-2 | 1 | 2 | 3 | 4 | 5 | 6 | 7 | 8 |
|---|---|---|---|---|---|---|---|---|
| A | 2.31 | 2.32 | 4.85 | 4.60 | 4.53 | 4.46 | 5.18 | 4.45 |
| B | 1.28 | 1.36 | 4.54 | 4.34 | 2.51 | 2.70 | 4.52 | 3.43 |
| C | 0.76 | 0.74 | 3.17 | 2.83 | 1.46 | 1.34 | 4.52 | 4.50 |
| D | 0.48 | 0.44 | 0.15 | 0.13 | 0.89 | 0.86 | 0.07 | 0.08 |
| E | 0.28 | 0.28 | 0.44 | 0.34 | 0.48 | 0.45 | 1.06 | 1.00 |
| F | 0.27 | 0.22 | 0.31 | 0.37 | 0.31 | 0.29 | 0.73 | 0.57 |
| G | 0.19 | 0.19 | 0.22 | 0.25 | 0.21 | 0.19 | 0.49 | 0.51 |
| H | 0.15 | 0.15 | 0.15 | 0.14 | 0.09 | 0.09 | 0.07 | 0.11 |

Figure 7:
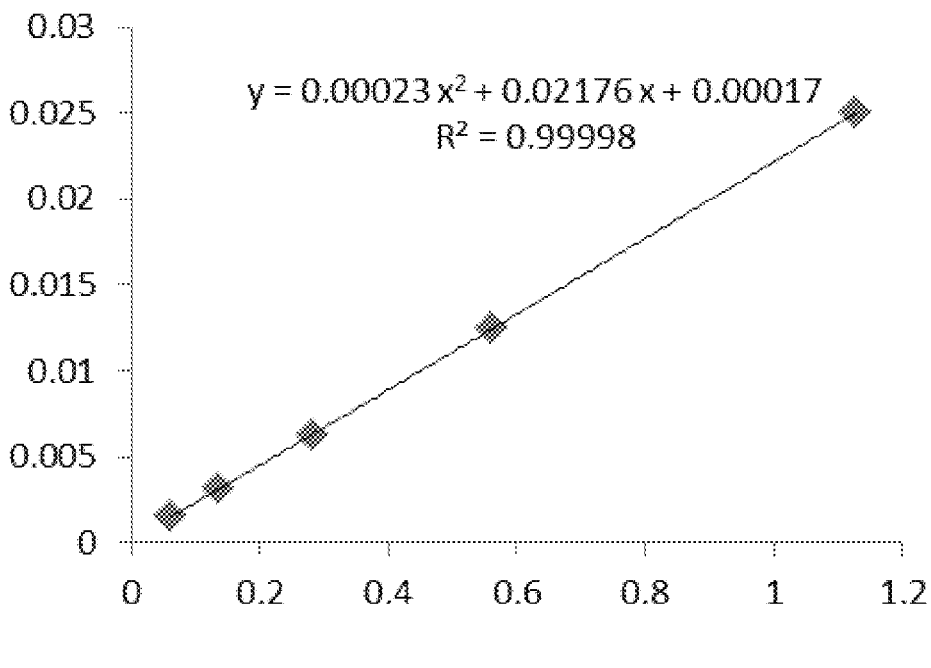
FIG. 7 is a corresponding standard curve diagram of an antibody pair 135 (4 µg/mL)-197 (0.5 µg/mL)
Figure 8:
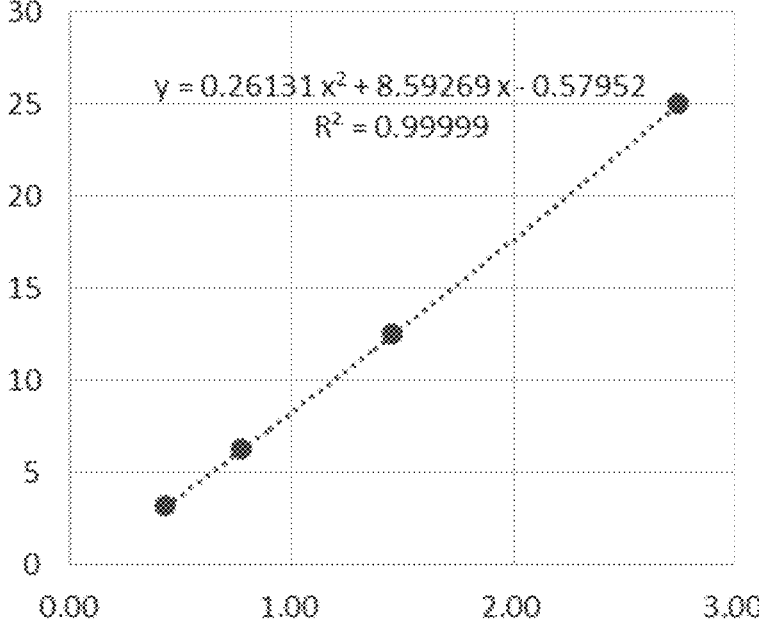
FIG. 8 is a corresponding standard curve diagram of an antibody pair 135 (4 µg/mL)-197 (0.25 µg/mL)
Figure 9:
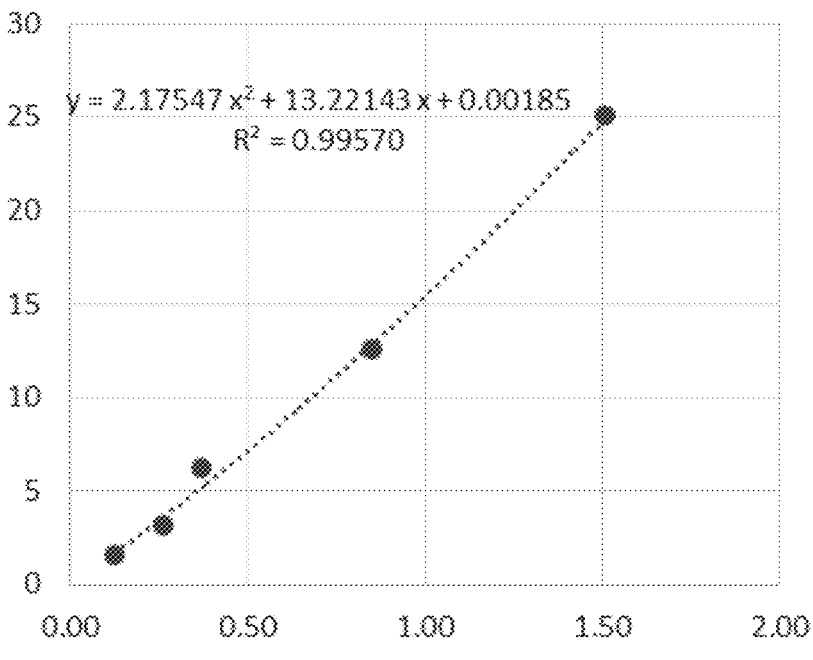
FIG. 9 is a corresponding standard curve diagram of an antibody pair 135 (2 µg/mL)-197 (0.25 ug/ml)
Figure 10:
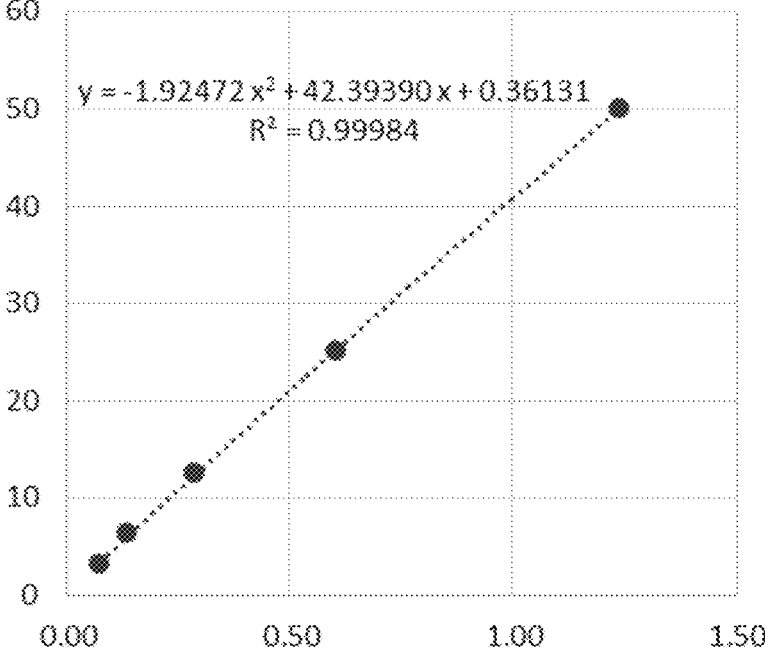
FIG. 10 is a corresponding standard curve diagram of an antibody pair 135 (1 ug/ml)-197 (0.25 µg/mL)
Figure 11:
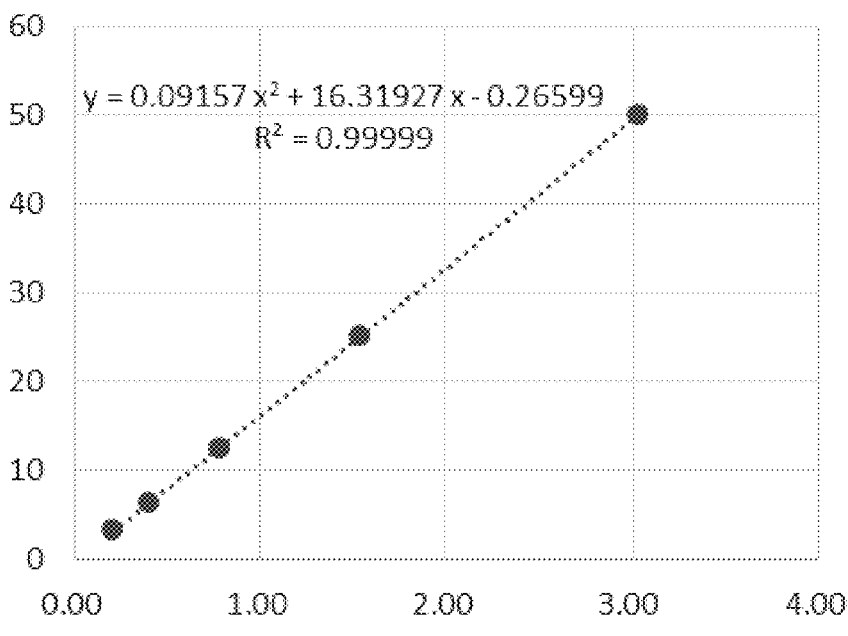
FIG. 11 is a corresponding standard curve diagram of an antibody pair 135 (4 µg/mL)-197 (0.125 µg/mL)
Figure 12:
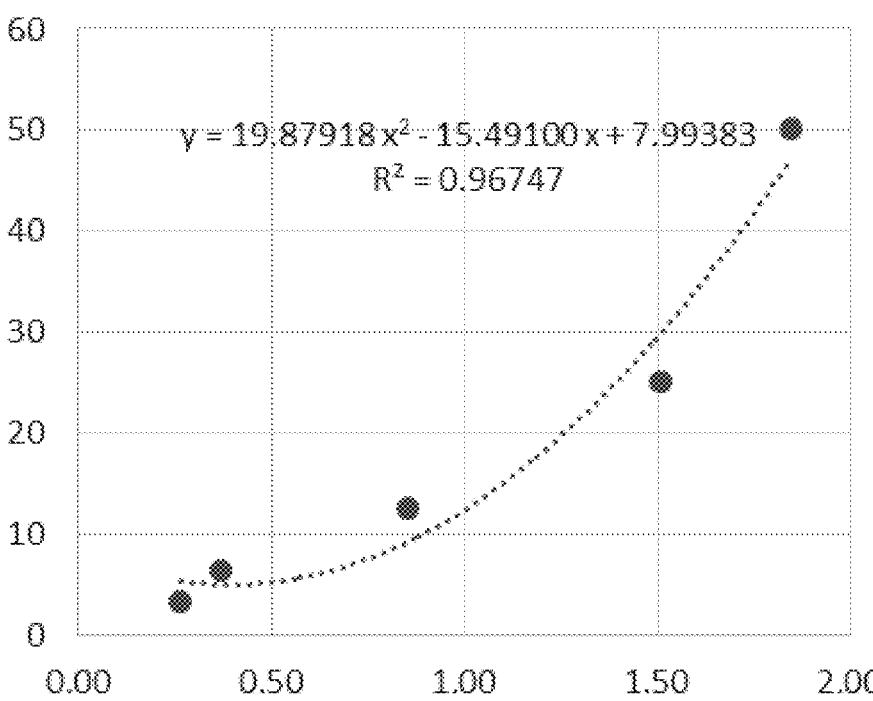
FIG. 12 is a corresponding standard curve diagram of an antibody pair 135 (2 µg/mL)-197 (0.125 µg/mL)
Figure 13:
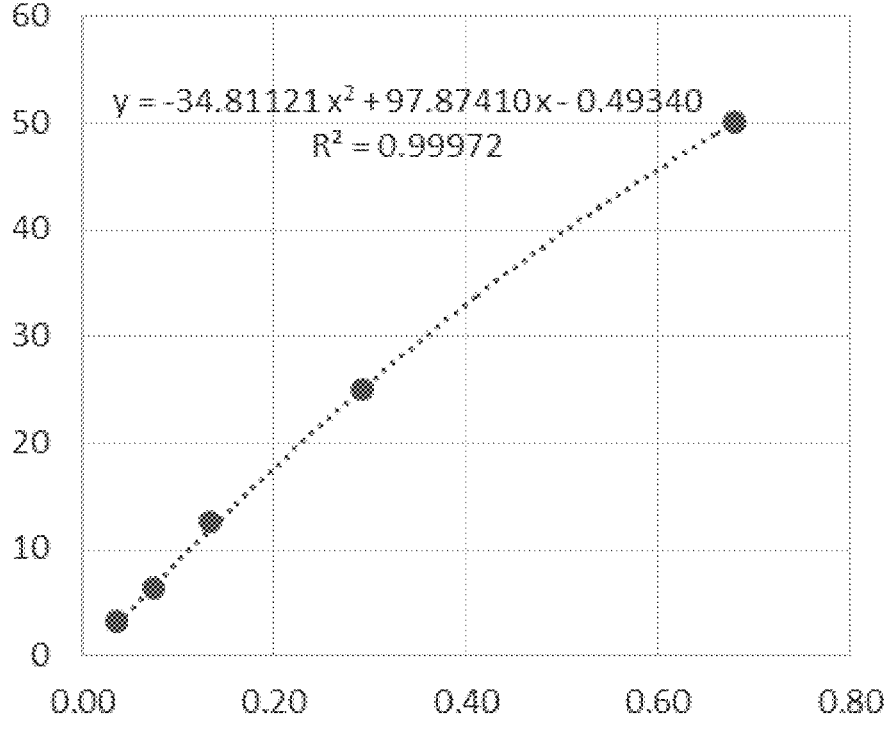
FIG. 13 is a corresponding standard curve diagram of an antibody pair 135 (1 µg/mL)-197 (0.125 µg/mL)

It can be seen from the data in Table 7 that the OD data in the blocks with shadows are decreased with the increase of the serum dilution multiple; and the corresponding antibody pair is 135 (4 µg/mL)-197 (0.5 µg/mL), and a corresponding standard curve is shown in Table 8 and FIG. 7:

TABLE 8

| Antibody 135 (4 ug/ml) | -blank | Antigen: (ug/ml) |
|---|---|---|
| 2.95 | 2.92 | 0.1000000 |
| 2.05 | 2.02 | 0.0500000 |
| 1.16 | 1.13 | 0.0250000 |
| 0.59 | 0.56 | 0.0125000 |
| 0.31 | 0.28 | 0.0062500 |
| 0.17 | 0.14 | 0.0031250 |
| 0.09 | 0.06 | 0.0015625 |
| 0.03 | 0.00 | 0.0000000 |
| 197bio (0.5 ug/ml) | | |

(4) The antibody pair 135 (4 µg/mL)-197 (0.5 µg/mL) was further optimized to determine the optimal working concentration of the antibody pair:

(1) optimization: three concentration gradients (4/2/1 µg/mL) were set for the capture antibody 135, three concentration gradients (0.5/1/2 µg/mL) were set for the detection antibody 197, and the protein PADI4 (subjected to doubling dilution from 50 ng/mL to 0.78125 ng/mL) was tested;

(2) optimization based on (1): one concentration gradient (4 µg/mL) was set for the capture antibody 135, two concentration gradients (0.25/0.125 µg/mL) were set for the detection antibody 197, and the protein PADI4 (subjected to doubling dilution from 50 ng/mL to 0.78125 ng/mL) was tested; and (3) optimization based on (2): three concentration gradients (4/2/1 µg/mL) were set for the capture antibody 135, two concentration gradients (0.25/0.125 µg/mL) were set for the detection antibody 197, and the protein PADI4 (subjected to doubling dilution from 50 ng/mL to 0.78125 ng/mL) was tested;

Date of each condition combination are shown in Table 9 to Table 14 and FIG. 8 to FIG. 13:

TABLE 9

| Antibody 135-197bio | Antibody 135 (4 ug/ml) | Antibody 135 (4 ug/ml) | average | -blank | Antigen: (ng/ml) |
|---|---|---|---|---|---|
| | 4.42 | 4.51 | 4.46 | 4.35 | 50 |
| | 2.83 | 2.90 | 2.86 | 2.75 | 25 |
| | 1.61 | 1.54 | 1.58 | 1.46 | 12.5 |
| | 0.93 | 0.85 | 0.89 | 0.77 | 6.25 |
| | 0.54 | 0.55 | 0.54 | 0.43 | 3.125 |
| | 0.29 | 0.34 | 0.32 | 0.20 | 1.5625 |
| | 0.24 | 0.25 | 0.24 | 0.13 | 0.78125 |
| | 0.12 | 0.11 | 0.12 | 0.00 | 0.0000000 |
| 197bio (0.25 ug/ml) | | | | | |

TABLE 10

| Antibody 135-197bio | Antibody 135 (2 ug/ml) | Antibody 135 (2 ug/ml) | average | -blank | Antigen: (ng/ml) |
|---|---|---|---|---|---|
| | 3.47 | 3.40 | 3.43 | 3.32 | 50 |
| | 1.91 | 1.34 | 1.62 | 1.51 | 25 |
| | 0.95 | 0.98 | 0.97 | 0.86 | 12.5 |
| | 0.51 | 0.46 | 0.49 | 0.37 | 6.25 |
| | 0.38 | 0.38 | 0.38 | 0.27 | 3.125 |
| | 0.23 | 0.25 | 0.24 | 0.13 | 1.5625 |
| | 0.18 | 0.19 | 0.18 | 0.07 | 0.78125 |
| | 0.11 | 0.12 | 0.11 | 0.00 | 0.0000000 |
| 197bio (0.25 ug/ml) | | | | | |

TABLE 11

| Antibody 135-197bio | Antibody 135 (1 ug/ml) | Antibody 135 (1 ug/ml) | average | -blank | Antigen: (ng/ml) |
|---|---|---|---|---|---|
| | 1.28 | 1.41 | 1.35 | 1.24 | 50 |
| | 0.64 | 0.77 | 0.71 | 0.60 | 25 |
| | 0.37 | 0.41 | 0.39 | 0.28 | 12.5 |
| | 0.23 | 0.25 | 0.24 | 0.13 | 6.25 |
| | 0.17 | 0.19 | 0.18 | 0.07 | 3.125 |
| | 0.14 | 0.13 | 0.14 | 0.03 | 1.5625 |
| | 0.13 | 0.12 | 0.12 | 0.02 | 0.78125 |
| | 0.10 | 0.11 | 0.11 | 0.00 | 0.0000000 |
| 197bio (0.25 ug/ml) | | | | | |

TABLE 12

| Antibody 135-197bio | Antibody 135 (4 ug/ml) | Antibody 135 (4 ug/ml) | average | -blank | Antigen: (ng/ml) |
|---|---|---|---|---|---|
| | 3.05 | 3.19 | 3.12 | 3.03 | 50 |
| | 1.64 | 1.61 | 1.63 | 1.53 | 25 |
| | 0.85 | 0.89 | 0.87 | 0.78 | 12.5 |
| | 0.50 | 0.49 | 0.50 | 0.41 | 6.25 |
| | 0.29 | 0.30 | 0.29 | 0.20 | 3.125 |

TABLE 12-continued

| Antibody 135-197bio | Antibody 135 (4 ug/ml) | Antibody 135 (4 ug/ml) | average | -blank | Antigen: (ng/ml) |
|---|---|---|---|---|---|
| | 0.19 | 0.19 | 0.19 | 0.09 | 1.5625 |
| | 0.15 | 0.15 | 0.15 | 0.06 | 0.78125 |
| | 0.09 | 0.09 | 0.09 | 0.00 | 0.0000000 |
| 197bio (0.125 ug/ml) | | | | | |

TABLE 13

| Antibody 135-197bio | Antibody 135 (2 ug/ml) | Antibody 135 (2 ug/ml) | average | -blank | Antigen: (ng/ml) |
|---|---|---|---|---|---|
| | 1.94 | 1.99 | 1.96 | 1.85 | 50 |
| | 1.02 | 0.95 | 1.62 | 1.51 | 25 |
| | 0.55 | 0.51 | 0.97 | 0.86 | 12.5 |
| | 0.27 | 0.29 | 0.49 | 0.37 | 6.25 |
| | 0.20 | 0.20 | 0.38 | 0.27 | 3.125 |
| | 0.14 | 0.14 | 0.24 | 0.13 | 1.5625 |
| | 0.13 | 0.12 | 0.18 | 0.07 | 0.78125 |
| | 0.08 | 0.08 | 0.11 | 0.00 | 0.0000000 |
| 197bio (0.125 ug/ml) | | | | | |

TABLE 14

| Antibody 135-197bio | Antibody 135 (1 ug/ml) | Antibody 135 (1 ug/ml) | average | -blank | Antigen: (ng/ml) |
|---|---|---|---|---|---|
| | 0.74 | 0.79 | 0.76 | 0.68 | 50 |
| | 0.35 | 0.41 | 0.38 | 0.29 | 25 |
| | 0.21 | 0.23 | 0.22 | 0.14 | 12.5 |
| | 0.15 | 0.17 | 0.16 | 0.08 | 6.25 |
| | 0.12 | 0.12 | 0.12 | 0.04 | 3.125 |
| | 0.10 | 0.10 | 0.10 | 0.01 | 1.5625 |
| | 0.09 | 0.10 | 0.09 | 0.01 | 0.78125 |
| | 0.08 | 0.09 | 0.08 | 0.00 | 0.0000000 |
| 197bio (0.125 ug/ml) | | | | | |

It can be found through comprehensive comparison of the data ($R^2$, OD corresponding to the same antigen concentration, and concentration (sensitivity) of the detection antibody) of the above six antibody pairs that the optimal working concentration of the antibody pair is as follows: Antibody 135 (4 µg/mL)-protein PADI4 (50 ng/mL to 0.78125 ng/mL)-197-bio (0.125 µg/mL).

Conclusions

The arrangements and the test data show that: according to OD of the positive serums and negative serums at 3 dilution multiples (1×, 2×, 4×), and the blank control, a ratio (minus the blank background value) of the positive serum OD to the negative serum OD at each dilution multiple was calculated, and results are shown in Table 15:

TABLE 15

| | 135-139biotin | | | 135-148biotin | | | 135~197biotin | | |
|---|---|---|---|---|---|---|---|---|---|
| Dilution multiple | + Serum OD-blank | – Serum OD-blank | +/– | + Serum OD-blank | – Serum OD-blank | +/– | + Serum OD-blank | – Serum OD-blank | +/– |
| 1X | 4.435 | 0.98 | 4.53 | 4.565 | 1 | 4.565 | 4.46 | 0.81 | 5.51 |
| 2X | 4.31 | 0.72 | 5.99 | 4.675 | 0.78 | 5.99 | 4.64 | 0.595 | 7.79 |
| 4X | 4.445 | 0.405 | 10.98 | 4.41 | 0.475 | 9.28 | 4.415 | 0.39 | 11.32 |

TABLE 15-continued

| Dilution multiple | 135-122biotin | | | 135-137biotin | | |
|---|---|---|---|---|---|---|
| | + Serum OD-blank | − Serum OD-blank | +/− | + Serum OD-blank | − Serum OD-blank | +/− |
| 1X | 4.585 | 0.245 | 4.34 | 4.74 | 0.94 | 5.04 |
| 2X | 4.3 | 0.195 | 22.00 | 3.9 | 0.56 | 6.96 |
| 4X | 2.86 | 0.09 | 31.70 | 4.435 | 0.41 | 10.81 |

Figure 14:
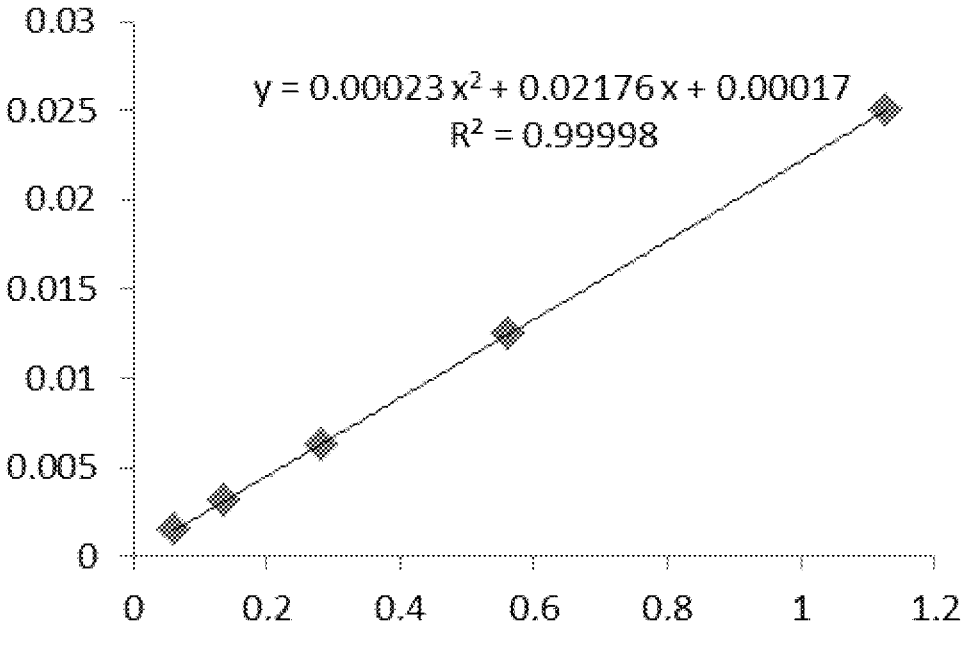
FIG. 14 is a corresponding standard curve diagram of an antibody pair 135-197biotin.
Figure 15:
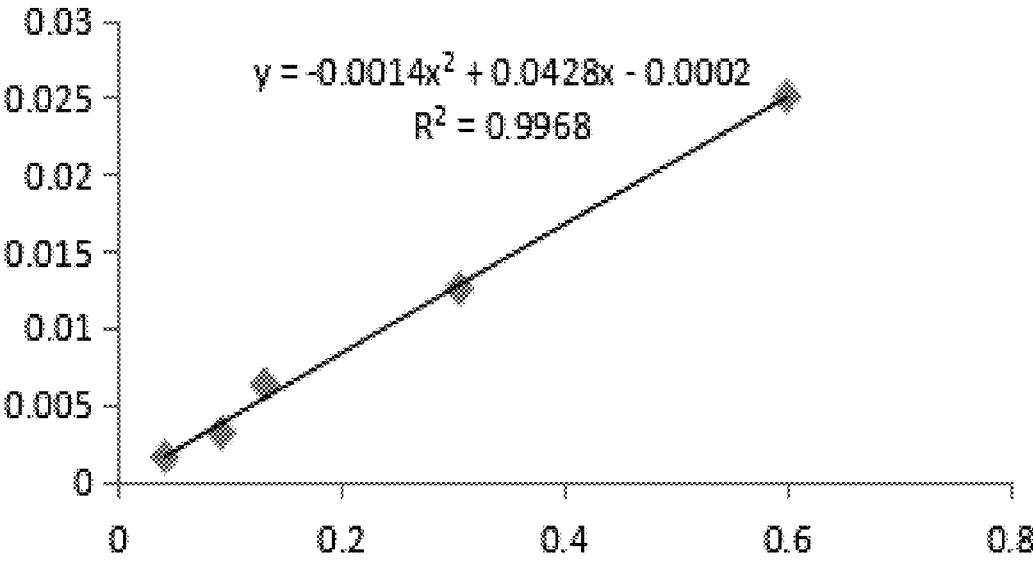
FIG. 15 is a corresponding standard curve diagram of an antibody pair 135-122biotin.

According to the comprehensive comparison of the above data, and OD of the protein PADI4, the protein PADI2 (for cross removal screening), the positive serums, and the negative serums that were respectively tested by each antibody pair, five groups of antibody pairs were determined; the five groups of antibody pairs are used to test serums at the same dilution, and through the comparison of the ratios (if the ratio is high, then the discrimination between the positive serum and the negative serum is good) of the positive serums to the negative serums of the antibody pairs, it is found that 135-197biotin and 135-122biotin are better, and the corresponding standard curves are shown in Table 16 and Table 17, and FIG. 14 and FIG. 15:

TABLE 16

| Antibody 135-197bio | Antibody 135 (4 ug/ml) | -blank | Antigen: (ug/ml) |
|---|---|---|---|
| | 2.95 | 2.92 | 0.1000000 |
| | 2.05 | 2.02 | 0.0500000 |
| | 1.16 | 1.13 | 0.0250000 |
| | 0.59 | 0.56 | 0.0125000 |
| | 0.31 | 0.28 | 0.0062500 |
| | 0.17 | 0.14 | 0.0031250 |
| | 0.09 | 0.06 | 0.0015625 |

TABLE 16-continued

| Antibody 135-197bio | Antibody 135 (4 ug/ml) | -blank | Antigen: (ug/ml) |
|---|---|---|---|
| | 0.03 197bio (0.5 ug/ml) | 0.00 | 0.0000000 |

TABLE 17

| Antibody 135-122bio | Antibody 135 (2 ug/ml) | Antibody 135 (2 ug/ml) | average | -blank | Antigen: (ug/ml) |
|---|---|---|---|---|---|
| | 2.31 | 2.32 | 2.32 | 2.17 | 0.1000000 |
| | 1.28 | 1.36 | 1.32 | 1.17 | 0.0500000 |
| | 0.76 | 0.74 | 0.75 | 0.60 | 0.0250000 |
| | 0.48 | 0.44 | 0.46 | 0.31 | 0.0125000 |
| | 0.28 | 0.28 | 0.28 | 0.13 | 0.0062500 |
| | 0.27 | 0.22 | 0.24 | 0.09 | 0.0031250 |
| | 0.19 | 0.19 | 0.19 | 0.04 | 0.0015625 |
| | 0.15 | 0.15 | 0.15 | 0.00 | 0.0000000 |
| | 122bio (2 ug/ml) | 122bio (2 ug/ml) | | | |

It is found through the comparison of the sensitivity (OD corresponding to the same antigen concentration) of the two antibody pairs and the relevance ($R^2$) of the standard curves that the antibody pair 135-197biotin is significantly better than the antibody pair 135-122biotin.

What is claimed is:

1. An antibody against a tumor antigen is antibody 135-B9 or antibody 197-A5; wherein the tumor antigen is peptidylarginine deiminase 4 protein; the antibody 135-B9 comprises one heavy chain having an amino acid sequence shown as SEQ ID NO: 3 and one light chain having an amino acid sequence shown as SEQ ID NO: 5; the antibody 197-A5 comprises two heavy chains having amino acid sequences shown as SEQ ID NO: 7 and SEQ ID NO: 9, respectively, and one light chain having an amino acid sequence shown as SEQ ID NO: 11.

2. The antibody according to claim 1, wherein the heavy chain of the antibody 135-B9 is expressed by a nucleic acid having a nucleotide sequence shown as SEQ ID NO: 4, and the light chain of the antibody 135-B9 is expressed by a nucleic acid having a nucleotide sequence shown as SEQ ID NO: 6.

3. The antibody according to claim 1, wherein the two heavy chains of the antibody 197-A5 are expressed by two nucleic acids having nucleotide sequences shown as SEQ ID NO: 8 and SEQ ID NO: 10, respectively, and the light chain of the antibody 197-A5 is expressed by a nucleic acid having a nucleotide sequence shown as SEQ ID NO: 12.

4. The antibody according to claim 1, wherein the tumor antigen is expressed by nucleic acid having a nucleotide sequence shown as SEQ ID NO: 2.

5. The antibody according to claim 1, wherein the antibody is used for detecting the tumor antigen in a biological sample.

6. The antibody according to claim 1, wherein the antibody is used for preparing as a tumor diagnostic kit with the tumor antigen, buffers and visualized reagents.

* * * * *